United States Patent
Wong et al.

(10) Patent No.: US 12,076,715 B1
(45) Date of Patent: Sep. 3, 2024

(54) SYNTHESIS AND CHARACTERIZATION OF AIR-STABLE IRON-BASED CATALYSTS FOR SUZUKI-MIYAURA CROSS-COUPLING REACTIONS OF ALKYL HALIDES AND ARYL BORONIC ESTERS

(71) Applicant: The Trustees of Boston College, Chestnut Hill, MA (US)

(72) Inventors: Alexander Wong, Brooklyn, NY (US); Jeffery Byers, Newton, MA (US)

(73) Assignee: THE TRUSTEES OF BOSTON COLLEGE, Chestnut Hill (MA)

( * ) Notice: Subject to any disclaimer, the term of this patent is extended or adjusted under 35 U.S.C. 154(b) by 0 days.

(21) Appl. No.: 17/721,133

(22) Filed: Apr. 14, 2022

Related U.S. Application Data

(60) Provisional application No. 63/175,388, filed on Apr. 15, 2021.

(51) Int. Cl.

| | |
|---|---|
| B01J 31/22 | (2006.01) |
| C07C 1/32 | (2006.01) |
| C07C 17/37 | (2006.01) |
| C07C 37/48 | (2006.01) |
| C07C 253/30 | (2006.01) |
| C07D 211/16 | (2006.01) |
| C07D 215/06 | (2006.01) |
| C07D 307/36 | (2006.01) |
| C07D 333/38 | (2006.01) |
| C07D 401/08 | (2006.01) |
| C07F 7/18 | (2006.01) |

(52) U.S. Cl.
CPC ........... *B01J 31/2234* (2013.01); *C07C 1/325* (2013.01); *C07C 17/37* (2013.01); *C07C 37/48* (2013.01); *C07C 253/30* (2013.01); *C07D 211/16* (2013.01); *C07D 215/06* (2013.01); *C07D 307/36* (2013.01); *C07D 333/38* (2013.01); *C07D 401/08* (2013.01); *C07F 7/1892* (2013.01); *B01J 2231/4211* (2013.01)

(58) Field of Classification Search
CPC .................................................. B01J 31/2234
See application file for complete search history.

(56) References Cited

PUBLICATIONS

Miyaura, et al., "A new stereospecific cross-coupling by the palladium-catalyzed reaction of 1-alkenylboranes with 1-alkenyl or 1-alkynyl halides" Tetrahedron Letters, 1979, pp. 3437-3440, vol. 36 (5 pages).
Brown, et al., "Analysis of Past and Present Synthetic Methodologies on Medicinal Chemistry: Where Have All the New Reactions Gone?" Journal of Medicinal Chemistry, 2016, vol. 59, pp. 4443-4458 (16 pages).
Choi et al., "Transition metal-catalyzed alkyl-alkyl bond formation: Another dimension in cross-coupling chemistry" Science, 2017, vol. 356, eaaf7230 (10 pages).
Han, "Transition-metal-catalyzed Suzuki-Miyaura cross-coupling reactions: a remarkable advance from palladium to nickel catalysts" Chem. Soc. Rev., 2013, vol. 42, pp. 5270-5298 (29 pages).
Balcells, et al., "Designing Pd and Ni Catalysts for Cross-Coupling Reactions by Minimizing Off-Cycle Species" ACS Catal. 2018, vol. 8, pp. 3499-3515 (17 pages).
Ananikov, "Nickel: The "Spirited Horse" of Transition Metal Catalysis" ACS Catal., 2015, vol. 5, pp. 1964-1971 (8 pages).
Zhou, et al., "Suzuki Cross-Couplings of Unactivated Secondary Alkyl Bromides and Iodides" J. Am. Chem. Soc., 2004, vol. 126, 1340-1341 (2 pages).
Zultanski, et al., "Nickel-Catalyzed Carbon-Carbon Bond-Forming Reactions of Unactivated Tertiary Alkyl Halides: Suzuki Arylations" J. Am. Chem. Soc., 2013, vol. 135, pp. 624-627 (4 pages).
Gonzalez-Bobes, et al., "Amino Alcohols as Ligands for Nickel-Catalyzed Suzuki Reactions of Unactivated Alkyl Halides, Including Secondary Alkyl Chlorides, with Arylboronic Acids" J. Am. Chem. Soc., 2006, vol. 128, pp. 5360-5361 (2 pages).
Kharasch, et al., "Factors Determining the Course and Mechanisms of Grignard Reactions. IV. The Effect of Metallic Halides on the Reaction of Aryl Grignard Reagents and Organic Halides" J. Am. Chem. Soc., 1941 (5 pages).
Tamura, et al. "Vinylation of Grignard Reagents. Catalysis by Iron" J. Am. Chem. Soc., Mar. 24, 1971, vol. 93, No. 6, 1487-1489 (3 pages).
Furstner, et al., "Iron-Catalyzed Cross-Coupling Reactions" J. Am. Chem. Soc., 2002, vol. 124, pp. 13856-13863 (8 pages).
Egorova, et al., "Toxicity of Metal Compounds: Knowledge and Myths" Organometallics, 2017, vol. 36, pp. 4071-4090 (20 pages).
Cahiez, et al., "Highly Stereo- and Chemoselective Iron-Catalyzed Alkenylation of Organomagnesium Compounds" Synthesis, Aug. 1998, pp. 1199-1205 (7 pages).
Furstner, et al., "Iron-Catalyzed Cross-Coupling Reactions of Alkyl-Grignard Reagents with Aryl Chlorides, Tosylates, and Triflates" Angew. Chem. Int. Ed., 2002, vol. 41, No. 4, pp. 609-612 (4 pages).
Nakamura, et al., "Iron-Catalyzed Cross-Coupling of Primary and Secondary Alkyl Halides with Aryl Grignard Reagents" J. Am. Chem. Soc., 2004, vol. 126, pp. 3686-3687 (2 pages).
Bisz, et al., "Iron-Catalyzed C(sp2)—C(sp3) Cross-Coupling of Chlorobenzenesulfonamides with Alkyl Grignard Reagents: Entry to Alkylated Aromatics" J. Org. Chem., 2019, vol. 84, pp. 1640-1646 (7 pages).
Lo, et al., "A Practical and Catalytic Reductive Olefin Coupling" J. Am. Chem. Soc., 2014, vol. 136, pp. 1304-1307 (4 pages).
Lo, et al., "Functionalized olefin cross-coupling to construct carbon-carbon bonds" Nature, 2014, vol. 516, pp. 343-348 (6 pages).
Lo, et al., "Fe-Catalyzed C—C Bond Construction from Olefins via Radicals" J. Am. Chem. Soc., 2017, vol. 139, pp. 2484-2503 (20 pages).
Kim, et al., "Roles of Iron Complexes in Catalytic Radical Alkene Cross-Coupling: A Computational and Mechanistic Study" J. Am. Chem. Soc., 2019, vol. 141, pp. 7473-7485 (13 pages).

(Continued)

*Primary Examiner* — John S Kenyon
(74) *Attorney, Agent, or Firm* — Morgan, Lewis & Bockius LLP

(57) ABSTRACT

This disclosure relates to novel catalysts for Suzuki-Miyaura cross-coupling reactions, the use thereof, and the methods of making the same.

20 Claims, 7 Drawing Sheets

(56) References Cited

PUBLICATIONS

Crockett et al., "Iron-Catalyzed Suzuki-Miyarua Cros-Coupling Reactions between Alkyl Halides and Unactivated Arylboronic Esters" Org. Lett., 2018, vol. 20, pp. 5233-5237 (5 pages).

Hatakeyama, et al., "Iron-Catalyzed Suzuki-Miyaura Coupling of Alkyl Halides" J. Am. Chem. Soc., 2010, vol. 132, pp. 10674-10676 (3 pages).

Bedford, et al., "Expedient Iron-Catalyzed Coupling of Alkyl, Benzyl and Allyl Halides with Arylboronic Esters" Chem. Eur. J., 2014, vol. 20, pp. 7935-7938 (4 pages).

O'Brien, et al., "Iron-catalysed substrate-directed Suzuki biaryl cross-coupling" Nature Catalysis, 2018, vol. 1, Jun. 2018, pp. 429-437 (9 pages).

Hedstrom, et al., "On the Radical Nature of Iron-Catalyzed Cross-Coupling Reactions" Chem. Eur. J., 2015, vol. 21, pp. 5946-5953 (8 pages).

Daifuku, et al., "A Combined Mossbauer, Magnetic Circular Dichroism, and Density Functional Theory Approach for Iron Cross-Coupling Catalysis: Electronic Structure, In Situ Formation, and Reactivity of Iron-Mesityl-Bisphosphines" J. Am. Chem. Soc., 2014, vol. 136, pp. 9132-9143 (12 pages).

Daifuku, et al., "Iron(II) Active Species in Iron-Bisphosphine Catalyzed Kumada and Suzuki-Miyaura Cross-Couplings of Phenyl Nucleophiles and Secondary Alkyl Halides" J. Am. Chem. Soc., 2015, vol. 137, pp. 11432-11444 (13 pages).

Tyrol, et al., "Iron-catalysed enantioconvergent Suzuki-Miyaura cross-coupling to afford enantioenriched 1,1-diarylalkanes" Chem. Commun., 2020, vol. 56, pp. 14661-14664 (4 pages).

Furstner, "Iron Catalysis in Organic Synthesis: A Critical Assessment of What It Takes to Make This Base Metal a Multitasking Champion" ACS Cent. Sci., 2016, vol. 2, pp. 778-789 (12 pages).

Crockett, et al., "Rational Design of an Iron-Based Catalyst for Suzuki-Miyaura Cross-Couplings Involving Heteroaromatic Boronic Esters and Tertiary Alkyl Electrophiles" Angew. Chem. Int. Ed., 2020, vol. 59, pp. 5392-5397 (6 pages).

Eckert, et al., "Low-Coordinate Iron(II) Amido Complexes of B-Diketiminates: Synthesis, Structure, and Reactivity" Inorganic Chemistry, 2004, vol. 43, No. 10, pp. 3306-3321 (16 pages).

Cowley, et al., "Three-Coordinate Terminal Imidoiron(III) Complexes: Structure, Spectroscopy, and Mechanism of Formation" Inorg. Chem., 2010, vol. 49, pp. 6172-6187 (16 pages).

Cowley, et al., "Selectivity and Mechanism of Hydrogen Atom Transfer by an Isolable Imidoiron(III) Complex" J. Am. Chem. Soc., 2011, vol. 133, pp. 9796-9811 (16 pages).

Cowley, et al., "Ligand Effects on Hydrogen Atom Transfer from Hydrocarbons to Three-Coordinate Iron Imides" Inorganic Chemistry, 2012, vol. 51, pp. 8352-8361 (10 pages).

Hu, et al., "Crystal structure of tris(acetylacetonato)iron(III), C15H21O6Fe, at 20 K" NCS, 2001, pp. 597-598 (2 pages).

Wertheim, et al., "Mossbauer Effect in Iron (III) Acetylacetonate and Chemical Consequences of K Capture in Cobalt (III) Acetylacetonate" J. Chem. Phys., 2004, vol. 37, pp. 687-690 (1962) (5 pages).

Korendovych, et al., "A New High-Spin Iron(III) Complex with a Pentadentate Macrocyclic Amidopyridine Ligand: A change from Slow Single-Ion Paramagnetic Relaxation to Long-Range Antiferromagnetic Order in a Hydrogen-Bonded Network" Inorg. Chem., 2004, vol. 43, pp. 3930-3941 (12 pages).

Evans, "The Determination of the Paramagnetic Susceptibility of Substances in Solution by Nuclear Magnetic Resonance" Chapter 400, 1959, pp. 2003-2005 (3 pages).

Ackermann, et al., "Air-Stable Secondary Phosphine Oxide or Chloride (Pre)Ligands for Cross-Couplings of Unactivated Alkyl Chlorides" Organic Letters, 2010, vol. 12, No. 10, pp. 2298-2301 (4 pages).

| Complex 2 | |
|---|---|
| Metric | Measurement |
| Fe1-N1 | 1.966 Å |
| Fe1-N2 | 1.957 Å |
| Fe1-Cl1 | 2.202 Å |
| Fe1-Cl2 | 2.183 Å |
| N1-Fe1-N2 | 94.92° |
| N1-Fe1-Cl1 | 107.90° |
| N2-Fe1-Cl2 | 115.02° |
| Cl1-Fe1-Cl2 | 116.19° |

| Complex 3 | |
|---|---|
| Metric | Measurement |
| Fe1-N1 | 2.065 Å |
| Fe1-N2 | 2.056 Å |
| Fe1-O1 | 2.038 Å |
| Fe1-O2 | 2.024 Å |
| Fe1-O3 | 2.041 Å |
| Fe1-O4 | 2.014 Å |
| N1-Fe1-N2 | 88.71° |
| O1-Fe1-O2 | 85.62° |
| O3-Fe1-O4 | 85.63° |

SYNTHESIS AND CHARACTERIZATION OF AIR-STABLE IRON-BASED CATALYSTS FOR SUZUKI-MIYAURA CROSS-COUPLING REACTIONS OF ALKYL HALIDES AND ARYL BORONIC ESTERS

CROSS REFERENCE TO RELATED APPLICATIONS

This application claims priority to U.S. Provisional Application No. 63/175,388, filed on Apr. 15, 2021, which is herein incorporated by reference in its entirety.

BACKGROUND OF THE INVENTION

Over the past four decades, the palladium-catalyzed Suzuki-Miyaura cross-coupling reaction has become a prominent and powerful tool for the assembly of $C(sp^2)$-$C(sp^2)$ bonds.[1] The impact of the Suzuki-Miyaura reaction is especially apparent in the pharmaceutical industry, where it is employed in nearly 25% of reported syntheses of medicinally active small molecule drugs.[2] Despite this impressive utility, cross-coupling reactions catalyzed by palladium-based complexes often undergo β-hydride elimination side reactions[3] and are often limited to $sp^2$-hybridized substrates, which in turn is likely an underlying reason for the disproportionate representation of mostly flat molecules in medicinally relevant small molecule drugs.[2] In order to explore the efficacy of pharmaceutical targets possessing three-dimensional features, first-row transition metal catalysis has emerged as a promising alternative. Of the first-row transition metals, nickel-based complexes have been most commonly investigated for cross-coupling catalysis;[4-9] in comparison, reactions catalyzed by iron-based complexes have historically received less attention,[10-12] despite the reduced cost and toxicity of iron when compared to that of palladium and nickel, respectively.[13] One challenge faced by iron catalysis in cross-coupling reactions is the propensity of iron-based catalysts to undergo rapid deactivation upon exposure to air or water, due to facile oxidation and hydrolysis reactions that form iron oxides. Bench-stable iron salts (e.g. $FeCl_3$, $Fe(acac)_3$) have been employed as catalyst precursors in cross-coupling reactions involving Grignard reagents[14-17] and alkenes[18-21], but their efficient activity towards boron-containing coupling partners remains elusive. Moreover, examples of Suzuki-Miyaura reactions catalyzed by iron-based complexes often require the use of reactive lithium amide bases[22] or substrates preactivated by highly pyrophoric alkyllithium bases.[23-25] Proposed catalytic cycles for these reactions often invoke the intermediacy of highly reactive and low-valent iron intermediates.[26-30] As a result, cross-coupling reactions catalyzed by iron-based catalysts usually demand the use of stringently air- and water-free conditions, which limit its practical implementation on scale. Therefore, there is a need to have air-stable catalysts with long term stability. The present invention meets such need.

SUMMARY OF THE INVENTION

The present invention is related to the synthesis and characterization of a new iron(III)-based catalyst that is stable and storable long-term on the benchtop and active for the cross-coupling of alkyl halides with arylboronic esters, as illustrated in FIG. 1b. In some embodiments, the catalyst disclosed herein are air-stable, and can be stored on the benchtop. In some embodiments, the catalyst disclosed herein are air-stable, and can be stored on the benchtop for at least one, two, three, four, five, six, seven, eight, or nine months while keeping its catalytic capability. In some embodiments, the catalyst disclosed herein are water-stable or moisture-stable.

In an embodiment, the present invention provides for an iron(III) catalyst for Suzuki-Miyaura cross-coupling reactions, wherein the catalyst has a composition according to Formula 1:

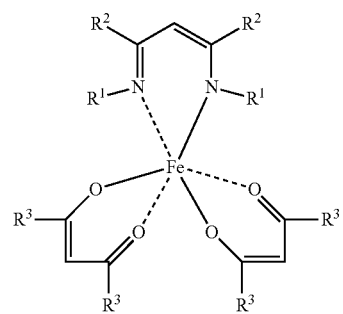

wherein each $R^1$ is independently selected from the group consisting of H, an alkyl group having 1 to 5 carbon atoms or phenyl and an alkyl substituted aryl group wherein the alkyl group has 1 to 5 carbon atoms; wherein each $R^2$ is independently selected from the group consisting of an alkyl group having 1 to 5 carbon atoms, phenyl, and an alkyl substituted aryl group wherein the alkyl group has 1 to 5 carbon atom; and each $R^3$ is independently selected from the group consisting of an alkyl group having 1 to 5 carbon atoms, phenyl, and an alkyl substituted aryl wherein the alkyl group has 1 to 5 carbon atoms. In such embodiments, the alkyl group of $R^1$, $R^2$ or $R^3$ is selected from the group consisting of methyl, ethyl, propyl, butyl, pentyl, isopropyl, neopentyl, tert-butyl, cyclopentyl, cyclopropyl, and $CF_3$. Further in such embodiments, the alkyl substituted aryl group is selected from the group consisting of 2,6-dialkyl, 3,5-dialkyl, and 2,4,6-trialkyl substituted aryl groups, and 2,4,6-trisubstituted aryl groups. For the dialkyl and trialkyl substituted aryl groups, the alkyl group is selected from the group consisting of methyl, ethyl, propyl, butyl, pentyl, isopropyl, neopentyl, tert-butyl, cyclopentyl, cyclopropyl, and $CF_3$. For the 2,4,6-trisubstituted aryl groups, substituents include 2,6-dialkyl substituents and a 4-substituent containing a halogen, an alkyl ether, and a dialkyl amine wherein the alkyl group is selected from the group consisting of methyl, ethyl, propyl, butyl, pentyl, isopropyl, neopentyl, tert-butyl, cyclopentyl, cyclopropyl, and $CF_3$. In one such embodiment, Formula 1 corresponds to:

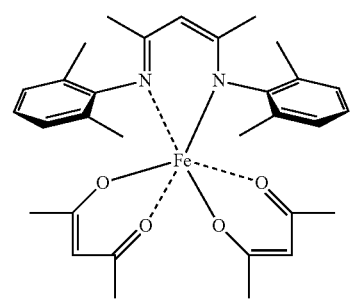

In another such embodiment, the iron(III) catalyst is stable in a solid state for a period of time selected from three to six months; three to nine months, six to nine months, each when stored in a desiccator.

In another embodiment, the present disclosure provides for a making an iron(III) catalyst for Suzuki-Miyaura cross-coupling reactions. The method includes the steps of: (a) preparing a solution of an Fe(acac)$_3$ complex; (b) reacting a β-diketimine compound with butyllithium to form a β-diketiminate; and (c) mixing the deprotonated β-diketiminate and the solution of an Fe(acac)$_3$ complex to form the iron(III) catalyst having a composition according to Formula 1. In one such embodiment, the β-diketimine compound is 2,4-bis[(2,6-dimethylphenyl)imino]pentane.

In yet another embodiment, the present invention provides for a method of catalyzing Suzuki-Miyaura cross-coupling reaction, comprising contacting a compound A of formula $R^A$—X and a compound B of formula $R^B$-G with the iron(III) catalyst having a composition according to Formula 1, wherein $R^A$ is an alkyl group; X is halogen or sulfonate ester of the formula OSO2R (R=tolyl, Me, CF$_3$; $R^B$ is an aryl and G is —B(OH)$_2$ or esters thereof. In such embodiments, $R^A$—X, the $R^A$ group may be any alkyl halide/pseudohalide, including CH$_3$, primary, secondary, and tertiary alkyl halides. Further in such embodiments, $R^B$-G (the boronic ester) can include any substituted aryl (unsubstituted, ortho substituted, meta substituted, and parasubstituted) boronic ester or heteroaryl boronic ester. Examples of heteroaryl boronic esters include indoles, pyridines, thiophenes, furans, and pyrizines. $R^B$-G may be an alkyl borane of the structure $R^B$ wherein the alkyl group may include CH$_3$, primary, secondary, and tertiary alkyl groups. In some embodiments, pseudohalide is selected from the group consisting of a sulfonate, a phosphate, a cyanide, an azide, an isocyanate, a thioisocyanate, and a quaternary nitrogen moiety.

In some embodiments, the present invention relates to a method of catalyzing Suzuki-Miyaura cross-coupling reaction, comprising contacting a compound A of formula $R^A$—X and a compound B of formula $R^b$-G with the iron(III) catalyst described herein, wherein $R^A$ is an alkyl group; X is halogen; $R^B$ is an aryl or heteroaryl; and G is B(OH)$_2$ or esters thereof.

In one such embodiment of catalyzing Suzuki-Miyaura reactions, the $R^A$—X group may be any alkyl halide/pseudohalide, including CH$_3$, primary, secondary, and tertiary alkyl halides; the $R^B$-G includes any substituted aryl (unsubstituted, ortho substituted, meta substituted, and parasubstituted) boronic ester or heteroaryl boronic ester or an alkyl borane.

DETAILED DESCRIPTION OF THE INVENTION

The present invention is directed to an iron(III) catalyst for Suzuki-Miyaura cross-coupling reactions. The iron(III) catalyst is air and water stable.

Figure 1A:
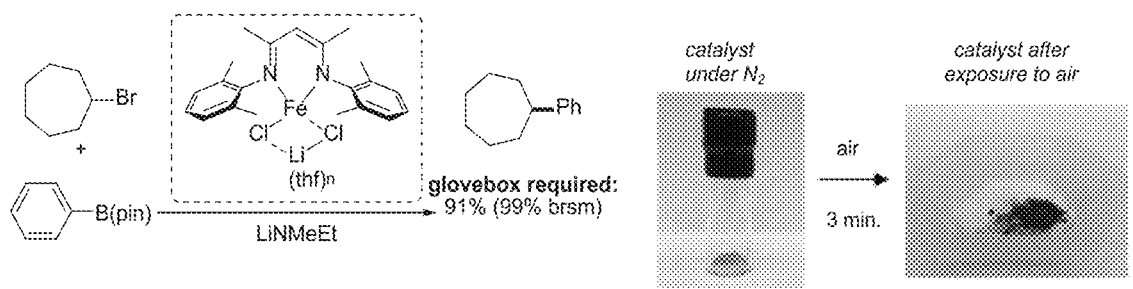
FIG. 1a illustrates the Suzuki-Miyaura cross-coupling of alkyl halides with aryl boronic esters catalyzed by iron-based complexes which required long-term storage and reaction setup in an air-free glovebox.
Figure 1B:
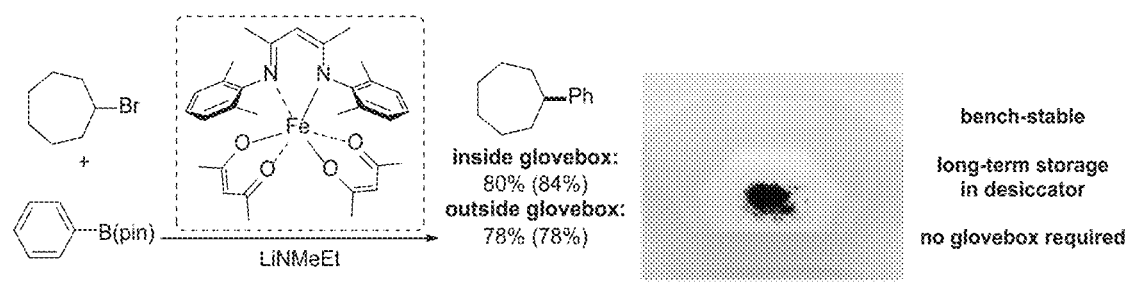
FIG. 1b illustrates an iron-based catalyst complex that is bench-stable and active for Suzuki-Miyaura cross-coupling reactions without the requirement of a glovebox.

To address the challenge mentioned in the background section of this disclosure, we have been developing iron-based catalysts for Suzuki-Miyaura cross-coupling reactions that have begun to address some of these limitations.[30] While these reactions no longer require pre-activation of boronic esters with alkyllithium reagents, they still required iron(II) catalyst precursors that prevented assembly of the reaction on the bench. We hypothesized that iron(III) catalyst precursors would be less prone to oxidation and hydrolysis compared to iron(II) catalyst precursors we have used previously (FIG. 1a). Additionally, following our current mechanistic understanding of the cross coupling reactions, we expect that the highly reducing conditions of the reaction would generate in situ the iron-(II)-based intermediates from air and water stable iron(III) precursors.

Without further elaboration, it is believed that one skilled in the art can, based on the above description, utilize the present invention to its fullest extent. The following specific embodiments and examples are, therefore, to be construed as merely illustrative, and not limitative of the remainder of the disclosure in any way whatsoever.

Definitions

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The term "H" denotes a single hydrogen atom. This radical may be attached, for example, to an oxygen atom to form a hydroxyl radical.

Where the term "alkyl" is used, either alone or within other terms such as "haloalkyl" or "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" or "alkylene" embraces bridging divalent alkyl radicals such as methylenyl or ethylenyl. The term "lower alkyl substituted with $R^2$" does not include an acetal moiety. The term "alkyl" further includes alkyl radicals wherein one or more carbon atoms in the chain is substituted with a heteroatom selected from oxygen, nitrogen, or sulfur.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, and butynyl, and the like.

Alkyl, alkylenyl, alkenyl, and alkynyl radicals may be optionally substituted with one or more functional groups such as halo, hydroxy, nitro, amino, cyano, haloalkyl, aryl, heteroaryl, and heterocyclo and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1 to 6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "aryl", alone or in combination, means a carbocyclic aromatic system containing one or two rings, wherein such rings may be attached together in a fused manner. The term "aryl" embraces aromatic radicals such as phenyl, naphthyl, indenyl, tetrahydronaphthyl, and indanyl. More preferred aryl is phenyl. An "aryl" group may have 1 or more substituents such as lower alkyl, hydroxyl, halo, haloalkyl, nitro, cyano, alkoxy, and lower alkylamino, and the like. Phenyl substituted with —O—CH$_2$—O— forms the aryl benzodioxolyl substituent.

The term "heterocyclyl" (or "heterocyclo") embraces saturated, partially saturated and unsaturated heteroatom-containing ring radicals, where the heteroatoms may be selected from nitrogen, sulfur and oxygen. It does not include rings containing —O—O—, —O—S— or —S—S— portions. The "heterocyclyl" group may have 1 to 4 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g., pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g., morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term heterocyclyl, (or heterocyclo) also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, and benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.
The term "heterocyclo" thus encompasses the following ring systems:
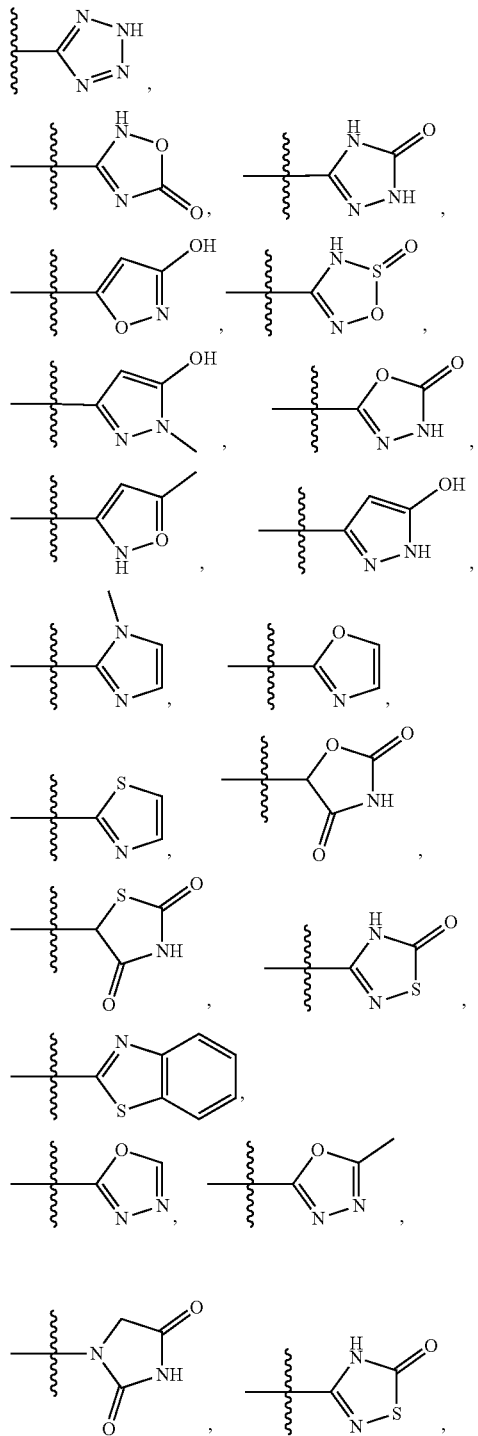
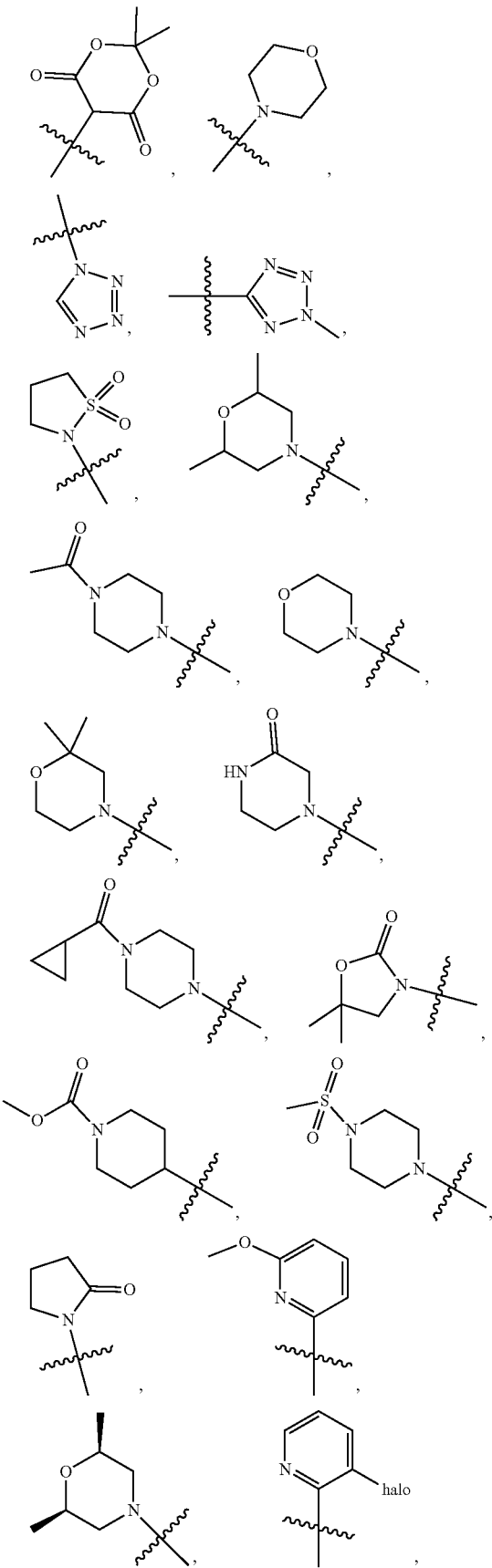

-continued

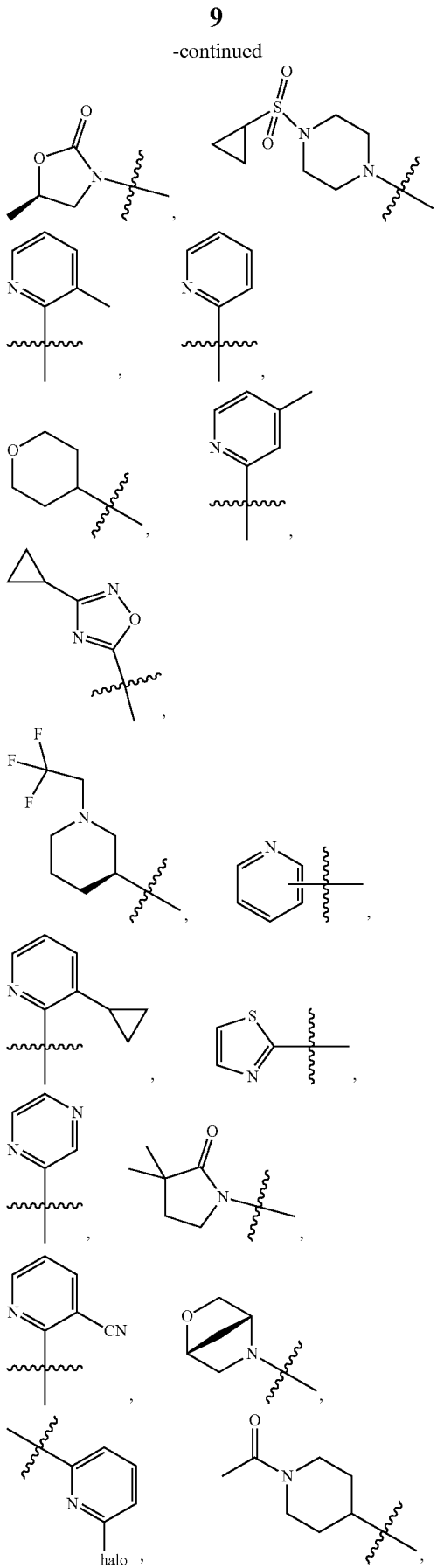

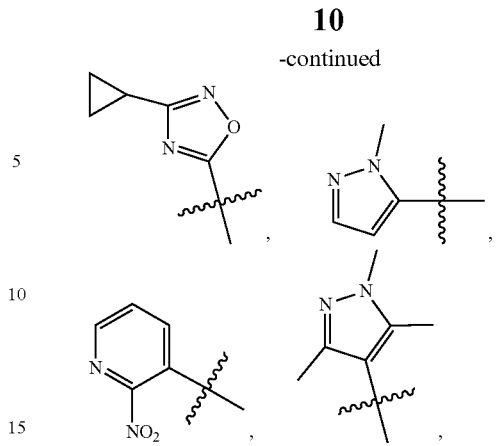

and the like.

The terms "carboxy" or "carboxyl," whether used alone or with other terms, such as "carboxyalkyl," denotes —CO$_2$H.

A group or atom that replaces a hydrogen atom is also called a substituent.

Any particular molecule or group can have one or more substituent depending on the number of hydrogen atoms that can be replaced.

The symbol "-" represents a covalent bond and can also be used in a radical group to indicate the point of attachment to another group. In chemical structures, the symbol is commonly used to represent a methyl group in a molecule.

Suzuki-Miyaura cross-coupling reaction is capable of assembling molecules with functionality common in many pharmaceuticals, such as functionalized heteroaromatic rings. It was also capable of carrying out difficult cross-coupling reactions, such as those involving tertiary alkyl halides. Utilizing these electrophiles in cross-coupling reactions result in the synthesis of all-carbon quaternary centers, a challenging motif to obtain for most synthetic methodologies. Despite their synthetic utility, the reactions required that discrete iron(II) complexes containing the β-diketiminate ligand be synthesized as opposed to reactions where ligands were added to iron-based catalyst precursors. These discrete complexes were not stable to oxygen or water, and rapidly (i.e. minutes) underwent decomposition when exposed to ambient air (FIG. 1a). Therefore, to obtain an air-stable catalyst precursor, we targeted discrete iron(III) catalyst precursors containing the β-diketiminate ligand.

Initially, we attempted to synthesize an iron(III) halide complex by using the iron(III) salt FeCl$_3$ in place of FeCl$_2$, but $^1$H NMR spectroscopy of the resulting product was identical to that of the previously used iron(II) complex 1. An effective magnetic moment measured in the solution-state for the product suggested that the iron(III) catalyst precursor was reduced in situ by the deprotonated ligand ($\mu_{eff}$=5.20) (Scheme 1a). We next attempted to oxidize the iron(II) complex with the addition of an external oxidant, ferrocenium hexafluorophosphate (Scheme 1b). An effective magnetic moment measured in the solution-state for the resultant purple crystals supported the successful oxidation to a high-spin iron(III) complex ($\mu_{eff}$=6.54), and the structure was confirmed by X-ray crystallographic characterization as the monomeric, neutral iron(III) dichloride complex 2 (FIG. 2, CCDC 2088833). Iron(III) halide complexes that contain the β-diketiminate ligand have not been previously reported. However, Holland and co-workers have previously synthesized four-coordinate β-diketiminate iron(III) amido complexes[32] that feature Fe—N bond lengths. These bond lengths are shorter than those reported for analogous four-coordinate iron(II) halide complexes,[31,32] which is consistent with an increase in oxidation state. In addition to the iron(III) halide complex 2, we also pursued the synthesis of the iron(III) complex 3. Since the iron(III) salt Fe(acac)$_3$ is often used as a bench-stable catalyst precursor and β-diketiminate ligands are isoelectronic and isolobal to acetylacetonate ligands, replacing an acetylacetonate ligand in Fe(acac)$_3$ with a β-diketiminate ligand could lead to an iron(III) complex containing the β-diketiminate ligand that was active for cross coupling catalysis and was air-stable. Addition of the deprotonated β-diketiminate ligand to Fe(acac)$_3$ resulted in the formation of a dark green compound 3 (Scheme 1c). An effective magnetic moment measured in the solution-state for complex 3 remains consistent with a high-spin iron(III) center ($\mu_{eff}$=7.04). X-ray crystallographic characterization of this complex confirmed the formation of an octahedral iron complex supported by one β-diketiminate ligand and two acetylacetonate ligands (FIG. 2b, CCDC 2088834). The Fe—N bond lengths of compound 3 are comparable to those found in previously reported β-diketiminate iron(II) complexes,[33] but longer than those found in previously reported β-diketiminate iron(III) complexes,[32-35] though the reported β-diketiminate iron(III) examples are limited to three- and four-coordinate iron(III) amido complexes. The Fe—O bond lengths of compound 3 are likewise longer than those found in Fe(acac)$_3$ (average bond length=1.991(8)Å).[36] The octahedral geometry of complex 3 also gives rise to a smaller N—Fe—N bond angle than that observed in other β-diketiminate iron(III) complexes, though the O—Fe—O bond angles are also smaller than those observed in Fe(acac)$_3$ (average O—Fe—O bond angle=87.47(3)°).[36] In comparison to 2, the Fe—N bond distances in 3 are significantly longer and the N—Fe—N bond angle is more acute.

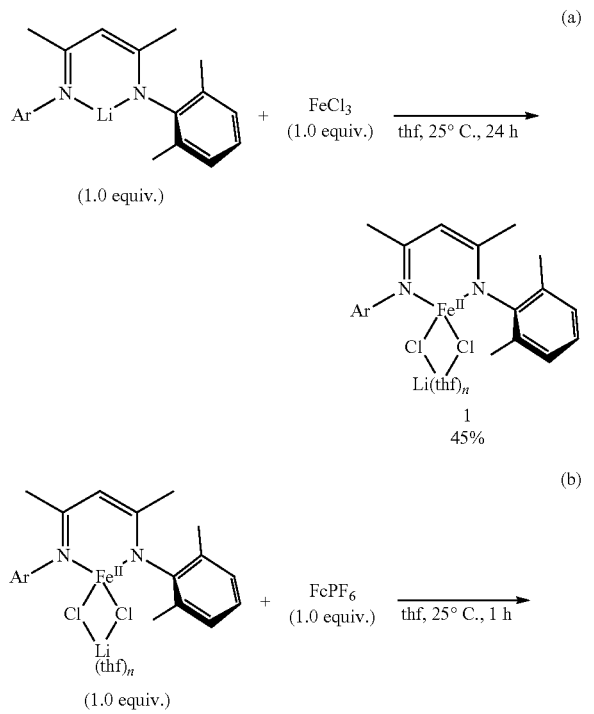

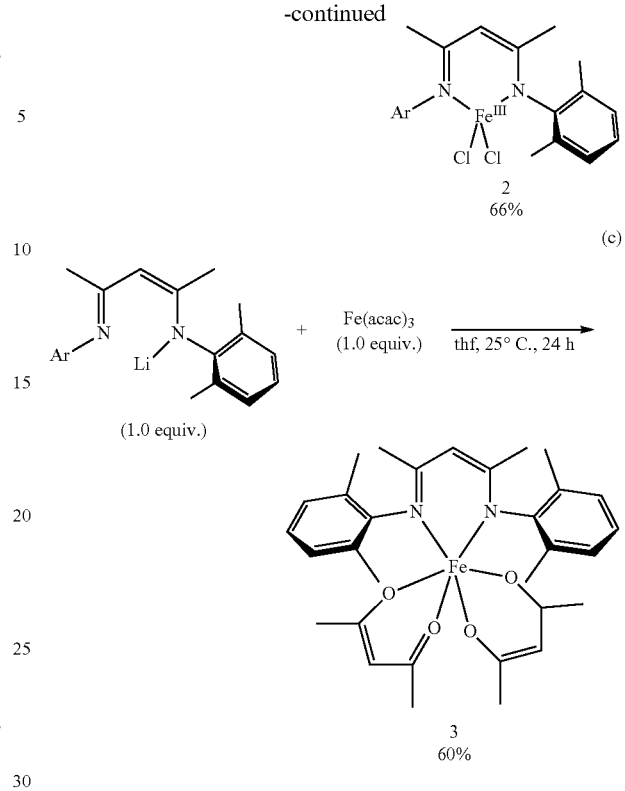

Scheme 1. a) Attempted synthesis of an iron(III) complex supported by a β-diketiminate ligand through the addition of FeCl$_3$, b) Synthesis of a neutral iron(III) dichloride complex supported by a β-diketiminate ligand via the oxidation of the analogous iron (II) complex, c) Synthesis of an air-stable iron(III) complex supported by a β-diketiminate ligand and two acetylacetonate (acac) ligands.

Table below illustrates X-ray crystal structures of complexes 2 and 3 with selected bond metrics. Thermal ellipsoids are drawn at the 50% probability level; co-crystallized solvent molecules and hydrogen atoms are omitted for clarity.

| Complex 2 | | Complex 3 | |
|---|---|---|---|
| Metric | Measurement | Metric | Measurement |
| Fe1-N1 | 1.966(6) Å | Fe1-N1 | 2.065(1) Å |
| Fe1-N2 | 1.957(6) Å | Fe1-N2 | 2.056(1) Å |
| Fe1-Cl1 | 2.202(2) Å | Fe1-O1 | 2.038(1) Å |
| Fe1-Cl2 | 2.183(3) Å | Fe1-O2 | 2.024(1) Å |
| N1-Fe1-N2 | 94.9(3)° | Fe1-O3 | 2.041(1) Å |
| N1-Fe1-Cl1 | 107.9(2)° | Fe1-O4 | 2.014(1) Å |
| N2-Fe1-Cl2 | 115.0(2)° | N1-Fe1-N2 | 88.71(5)° |
| Cl1-Fe1-Cl2 | 116.2(1)° | O1-Fe1-O2 | 85.62(4)° |
| | | O3-Fe1-O4 | 85.63(5)° |

Figure 7:
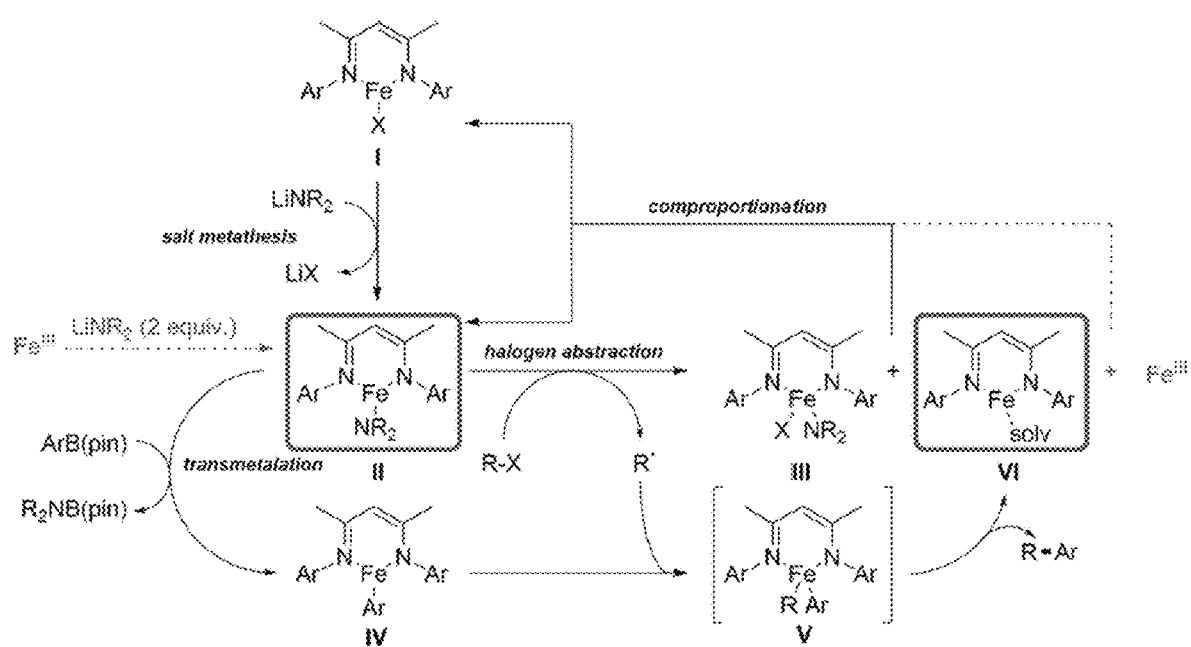
FIG. 7 illustrates mechanistic hypothesis for the cross-coupling reaction of alkyl halides and aryl boronic esters catalyzed by β-diketiminate iron(II) complexes.

When complex 1 was subjected to our standard cross-coupling conditions following its exposure to in air for one hour, the Suzuki-Miyaura reaction between bromocycloheptane and phenyl boronic acid pinacol ester produced phenylcycloheptane in significantly reduced yield (15% as an average of five trials, compared to 91% without air exposure). Conversely, an initial attempt to subject complex 2 to our standard cross-coupling conditions following exposure to air for one hour delivered the product in 60% yield (compared to 85% without air exposure), and complex 3 delivered the product in 78% yield (compared to 87% without air exposure) under the same conditions. We have previously proposed a catalytic cycle for the iron(II)-catalyzed Suzuki-Miyaura cross-coupling reaction, which is our current working mechanistic hypothesis for the cross coupling reaction[29]. In this proposed mechanism, iron(II) halide catalyst I is activated by salt metathesis with the lithium amide base (FIG. 7). Iron(II) amide species II activates the electrophile and the nucleophile via halogen abstraction to yield intermediate IIIa and transmetalation to yield intermediate IIIb, respectively. The carbon-centered radical formed by halogen abstraction recombines with III, followed by reductive elimination from IV to deliver the cross-coupled product. Finally, catalyst turnover is achieved by comproportionation between IIIa and V to regenerate an equivalent of I and an equivalent of II. We hypothesized that the presence of a strong reductant like lithium amide could enable the iron(III) precursors to enter the catalytic cycle as presumably iron(II) amide species II. Alternatively, the iron(III) precursors could participate in comproportionation with the low-coordinate iron(I) species V generated from reductive elimination to enter the catalytic cycle.

With the competency of an iron(III) catalyst for Suzuki-Miyaura cross-coupling established, we next sought to assess the benchtop stability of the iron complexes. The $^1$H NMR spectrum of iron chloride complex 2 displayed no change immediately following exposure to air, which is consistent with our working hypothesis that these compounds would be less sensitive to oxidation. However, further exploration revealed that 2 was not indefinitely stable to air because a color change of the sample accompanied by loss of all paramagnetic resonances in the $^1$H NMR were observed within 24 hours after initial exposure to air. This finding suggested that catalyst deactivation occurred. Conversely, complex 3 remained stable in the solid-state for up to nine months following its storage in a benchtop desiccator, as determined by $^1$H NMR spectroscopy.

Figure 4A:
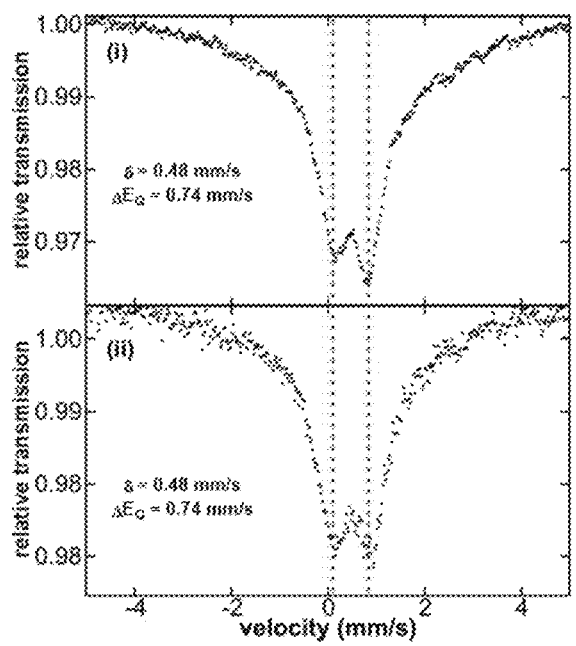
FIG. 4a illustrates a comparison of the 80 K $^{57}$Fe Mössbauer spectra of iron(III) catalyst complex 3, i) prior to and ii) following exposure to air.

To gain further insight, the speciation of the iron center in complex 3 was also examined using $^{57}$Fe Mössbauer spectroscopy. The 80 K $^{57}$Fe Mössbauer spectrum of a powder of iron(III) complex 3 features a broad doublet with Mössbauer parameters of $\delta$=0.47 mm/s and $|\Delta E_Q|$=0.82 mm/s, consistent with a high-spin iron(III) species (FIG. 4a). Most importantly, the spectrum of a sample of 3 taken after four months of continued exposure to air displayed no substantial changes from that of a freshly synthesized sample of the same complex. A similar analysis of the iron(II) complex 1 before and after only one hour of exposure to air (FIG. 4b) displayed marked differences in the Mössbauer spectra that suggest near-complete conversion of the iron(II) complex ($\delta$=0.90 mm/s and $|\Delta E_Q|$=2.41 mm/s) to a mixture of iron complexes, the two major components of which have Mössbauer parameters ($\delta$=0.42 mm/s and $|\Delta E_Q|$=0.81 mm/s, 48% of total iron, blue component; $\delta$=0.38 mm/s and $|\Delta E_Q|$=1.37 mm/s, 46% of total iron, red component) consistent with iron(III) complexes formed from rapid oxidation. This rapid oxidation is further supported from changes in the $^1$H NMR spectrum of the complex as well as its physical appearance. These changes are also consistent with the decreased yield observed for reactions where complex 1 was exposed to air for one hour compared to reactions carried out entirely in the glovebox (vide supra).

These sets of experiments demonstrate that the iron(III) complex 3 is less prone to degradation in air, and is less prone to decomposition on the benchtop than iron(II) catalyst precursors. In addition to oxidation state, we speculate that the iron(II) halide complex 1 is less stable to air than iron(III) complex 3 due to more rapid hydrolysis of iron halides compared to iron acetylacetonate complexes. This hypothesis is also consistent with the observed behavior of complex 2, which is an iron(III) halide complex that rapidly undergoes deactivation towards cross-coupling at room temperature, presumably because hydrolysis rather than oxidation occurs. Thus, with the proper choice of oxidation state and supporting ligands, air- and moisture-stable catalyst precursors for the Suzuki-Miyaura cross-coupling reaction were obtained.

Having demonstrated the benchtop stability of the iron-based complex, we sought to evaluate conditions for the catalytic cross-coupling reaction in hopes of eliminating the need to use a glovebox for the reaction (Table 1A). Low yields were obtained when the reaction was carried out with commercially available Fe(acac)$_3$ and $\beta$-diketiminate ligand in place of iron complex 3 synthesized prior to the cross-coupling reaction (Table 1A, entry 1). All other reactions reported in Table 1A were carried out with iron complex 3 that was exposed to air for at least 4 weeks. The yield obtained after 4 weeks of exposure to air (56±1%) was lower than the yield of the reaction carried out after 1 h of exposure to air (71±11%). However, increasing the equivalents of the base to 2 resulted in better yields (80±6%) compared to when 1.2 equiv of the base were used (Table 1A, entries 2-6). Further investigation revealed that reactions carried out with 2.0 equiv of base were best to obtain reproducible yields regardless of how long complex 3 was exposed to air: complex 3 that was not exposed to air gave a nearly identical yield (83±6%) as the reaction carried out after 3 was exposed to air for 4 weeks, and a reaction carried out after complex 3 had been exposed to air for 9 months delivered the cross-coupled product in 79% yield. Reactions run with 2 equiv of base proved to be optimal to obtain high yields reproducibly because further increasing the equivalents of base led to lower isolated yields (Table 1A, entries 5 and 6). Cognizant of the toxicity of benzene as an ICH class 1 solvent, 39 more environmentally friendly solvents like 2-methyl tetrahydrofuran and anisole (both class 3 solvents) were also evaluated for the reaction (Table 1A, entries 7 and 8). While reactions carried out in 2-methyl tetrahydrofuran led to a slight drop in yield compared to reactions carried out in benzene, reactions in anisole gave almost the same yield as reactions in benzene. While benzene was used as the primary solvent for the remainder of this study due to its relative ease of removal from the reaction mixture, we anticipate that anisole can be used as a replacement for benzene industrially.

TABLE 1A

Optimization of reaction conditions

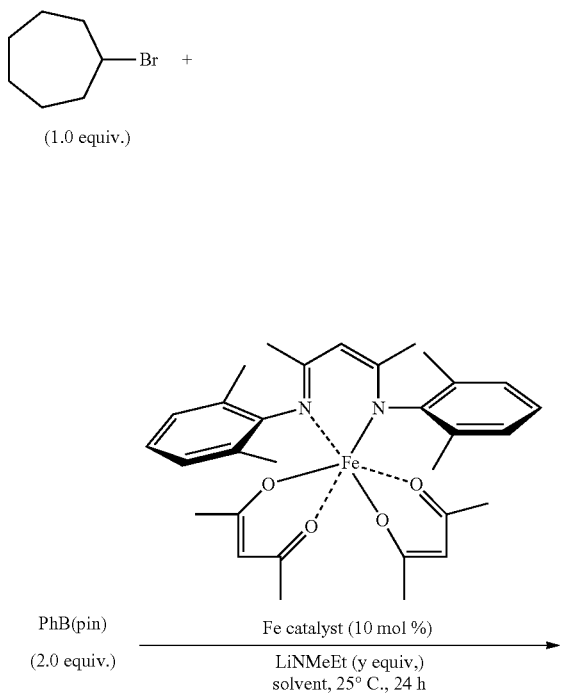

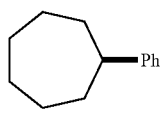

| entry | LiNMeET (equiv) | solvent | yield (%) glovebox[a] | yield (%) Schlenk line[a] |
|---|---|---|---|---|
| 1[b] | 1.2 | benzene | 24[c] | n/a |
| 2 | 1.2 | benzene | 56 (±1)[c] | 40[d] |
| 3 | 1.5 | benzene | 66[c] | 43[d] |
| 4 | 2.0 | benzene | 80 (±6)[c,f] | 66 (±4)[d,f] |
| 5 | 2.5 | benzene | 45[c] | 52[d] |
| 6 | 3.0 | benzene | 22[c] | 0[d] |
| 7 | 2.0 | 2 MeTHF | 69[c] | 49[d] |
| 8[e] | 2.0 | anisole | 78[c] | 22[d] |
| 9[e] | 2.0 | 1:6 anisole:benzene | 99[c] | 69[d] |
| 10[e] | 2.0 | 1:6 anisole:benzene | n/a | 74 (±3)[f] |
| 11 | 2.0 | benzene | n/a | 90[c] |

[a] See Experimental Section for details regarding reaction assembly. [b] Fe(acac)$_3$ combined with β-diketiminate ligand in place of discrete catalyst. [c] LiNMeEt added as a uniformly sieved solid. [d] LiNMeEt added as a dispersion in anisole. [e] LiNMeEt synthesized in anisole in reaction vessel immediately prior to addition of catalyst and substrates. [f] average of five trials. [g] Unless otherwise stated, the iron catalyst was exposed to air for 4 weeks prior to the reaction.

TABLE 1B

Further optimization of reaction conditions

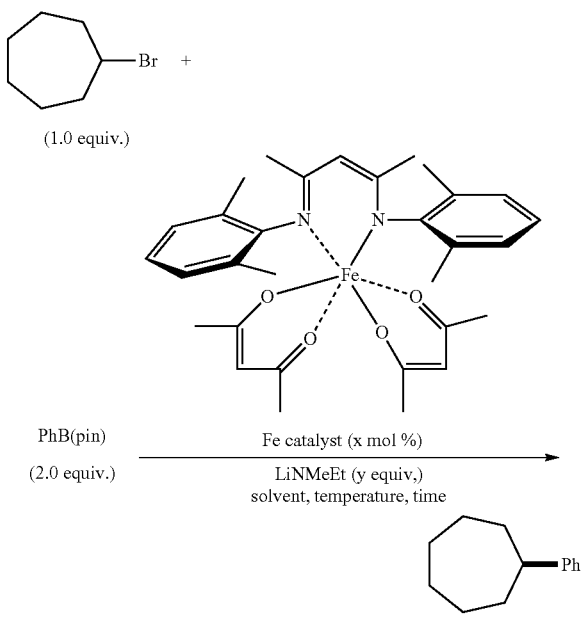

| entry | x (cat. loading) | y (equiv. base) | base | solvent | temp. (° C.) | time (h) | yield (brsm) |
|---|---|---|---|---|---|---|---|
| 1[a] | 10 | 1.2 | LiNMeEt | benzene | 25 | 48 | 36 (58) |
| 2[a] | 20 | 1.2 | LiNMeEt | benzene | 25 | 24 | 46 (62) |
| 3[a] | 10 | 1.2 | LiNMeEt | benzene | 50 | 24 | 17 (27) |
| 4[a] | 10 | 1.2 | LiNMeBu | benzene | 25 | 24 | 26 (41) |
| 5[a] | 10 | 1.2 | LiNMeBu | benzene | 25 | 48 | 20 (32) |
| 6[a] | 20 | 1.2 | LiNMeBu | benzene | 25 | 24 | 43 (75) |
| 7[a] | 10 | 2.0 | LiNMeEt | benzene | 50 | 24 | 94 (94) |
| 8[b] | 10 | 2.0 | LiNMeEt | anisole | 50 | 24 | 84 (84) |
| 9[b] | 10 | 2.0 | LiNMeEt | anisole | 80 | 24 | 85 (85) |
| 10[c] | 10 | 2.0 | LiNMeEt | benzene | 25 | 24 | 0 (0) |
| 11[c] | 10 | 2.0 | LiNMeEt | benzene[d] | 25 | 24 | 47 (60) |
| 12[c] | 10 | 2.0 | LiNMeEt | 1:6 anisole:benzene[e] | 25 | 24 | 36 (47) |
| 13[c] | 10 | 2.0 | LiNMeEt | anisole | 25 | 24 | 38 (38) |

[a] Schlenk line setup, LiNMeEt added as a dispersion in anisole. [b] Glovebox setup. [c] LiNMeEt synthesized via deprotonation of HNMeEt with n-butyllithium in reaction vessel immediately prior to addition of catalyst and substrates. [d] deprotonation occurred in pentane, which was removed before addition of substrates and catalyst. [e] deprotonation occurred in pentane, which was removed and replaced with anisole before addition of substrates and catalyst.

Our previous results suggest that using a lithium amide base is helpful for iron-catalyzed cross-coupling reactions to avoid the irreversible formation of inactive iron aggregates.[22] Unfortunately, using alkyl amide bases precludes a facile reaction setup on the benchtop.[40] Because lithium amide is moderately soluble. in anisole and employing anisole as a solvent did not adversely affect the outcome of the reaction in the glovebox, a procedure was developed which involved dispensing a dispersion of lithium amide in anisole into the reaction vessel for application on the Schlenk line. Reaction setup using this procedure produced the desired product, although the lower yield was generally observed compared to reactions setup and carried out inside of a glovebox with the same solvent ratio (Table 1A, entry 9). Higher yields could be obtained by deprotonating the amine with n-butyllithium in anisole in the reaction vessel on the Schlenk line immediately prior to the addition of the catalyst and substrates under a positive flow of inert gas (Table 1A, entry 10). Employing this procedure, yields were comparable to reactions assembled in the glovebox and employing benzene as the solvent (cf. Table 1A, entry 4). Using this procedure, the reaction could be performed on a gram scale, enabling isolation of the desired cross-coupled product in 82% yield.

It is important to mention that discrepant yields obtained between the reactions carried out in the glovebox and on Schlenk lines are chiefly due to the manner in which lithium amide is added to the reaction mixture, rather than the air sensitivity of the catalyst precursor or the fidelity of the air-free procedure. To illustrate this fact, the cross-coupling reaction was carried out using solid lithium amide that was sieved so that the particle size introduced to the reaction was 250 μm or smaller (Table 1A, entry 11). Lithium amide prepared in this way was then weighed into a sealed reaction vessel inside a glovebox, which was evacuated on a Schlenk line prior to the addition of complex 3, reaction substrates, and the solvent (weighed out/dispensed on the bench) under a positive pressure of inert gas. The product yield was comparable to those from reactions using complex 1 inside of a glovebox (96%, vide supra), which also employed sieved lithium amide rather than an in situ suspension in anisole. We hypothesize that lithium amide benefits from being sieved because it helps regulate lithium amide dissolution, which is only partially soluble in the aromatic solvents used. Consequently, the partial solubility of the base in aromatic solvents is beneficial to carrying out the reaction in benzene and anisole rather than 2-methyl tetrahydrofuran because these solvents provide a convenient way to gradually introduce the base to the reaction as it proceeds.

While the reaction involving sieved lithium amide gave superior yields, this procedure required the use of a glovebox. Thus, using the optimal procedure that does not require a glovebox (i.e., the procedure that involves deprotonation of the amine in situ), the substrate scope of the reaction was explored next (Table 2). Heteroaromatic-containing substrates 4-10, which were amenable to our previously reported method, 31 were also viable for cross-coupling with the air-stable catalyst. These substrates are highly represented in pharmaceutically relevant compounds and demonstrate how the new protocol may have value to medicinal and process chemists. Primary, secondary, and tertiary alkyl halides 11-16 were well-tolerated, as well as protected amine 17 and a protected alcohol 18. While the need for the lithium amide base somewhat limited the functional group tolerance of the method (e.g., esters, ketones, and free amines were not tolerated), an alkyl halide containing a nitrile resulted in some cross-coupled product 19. All reactions delivered the desired cross-coupled product regardless of whether they were assembled in the glovebox or on the Schlenk line, although lower product yield is generally observed when compared to analogous reactions using the previously reported β-diketiminate iron(II) catalyst precursors in the glovebox (see Table 1B). However, to emphasize that discrepant yields are chiefly due to the manner in which lithium amide is added to the reaction mixture and not the air sensitivity of the catalyst precursor nor the inability for the iron(III) precursor to be reduced to the catalytically active species, the procedure using solid lithium amide that was sieved prior to addition of 3 and the other reagents using the Schlenk line as described in Table 1, entry 11 was tested for substrate 10 to obtain the product in 67% yield, which was similar to the 68% yield obtained when using complex 1 inside of a glovebox.

Table 2. a) Substrate scope for cross-coupling reactions performed without the aid of a glovebox using air-stable complex 3 as a catalyst precursor. Isolated yields are reported with yields based on recovered starting material in parentheses. Yields from reactions employing the iron(II) catalyst 1 in the glovebox are reported below in italics. b) Cross-coupling reactions performed without the aid of a glovebox using uniformly sieved lithium amide and complex 3 as catalyst precursor.

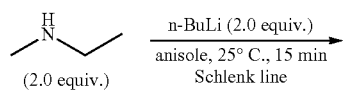

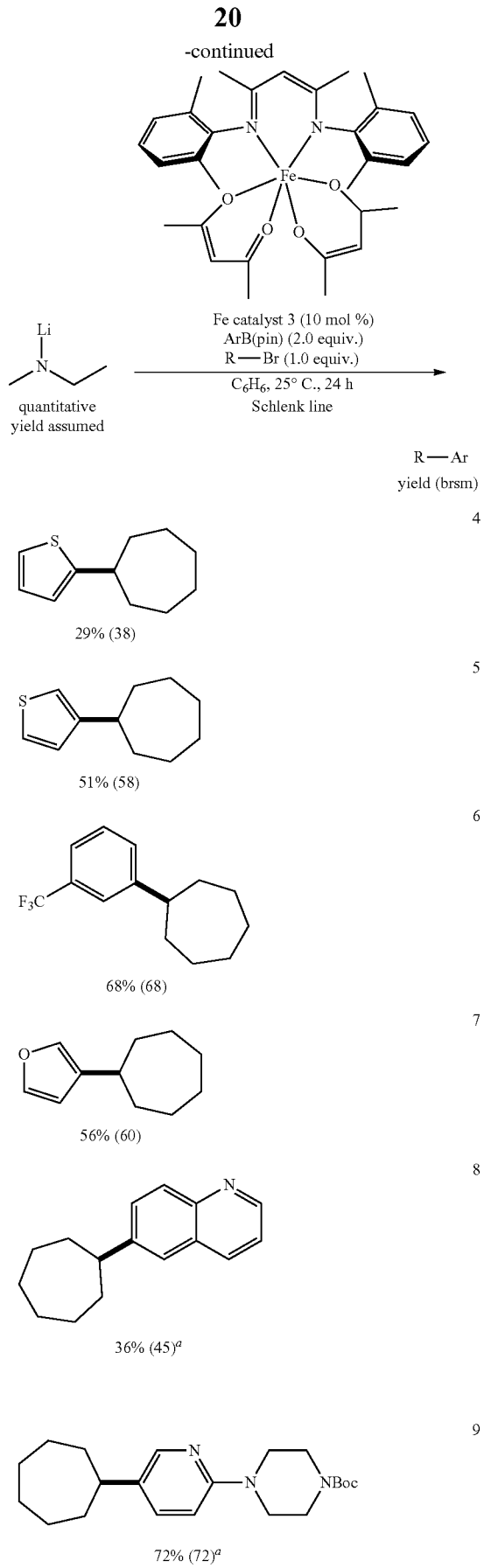

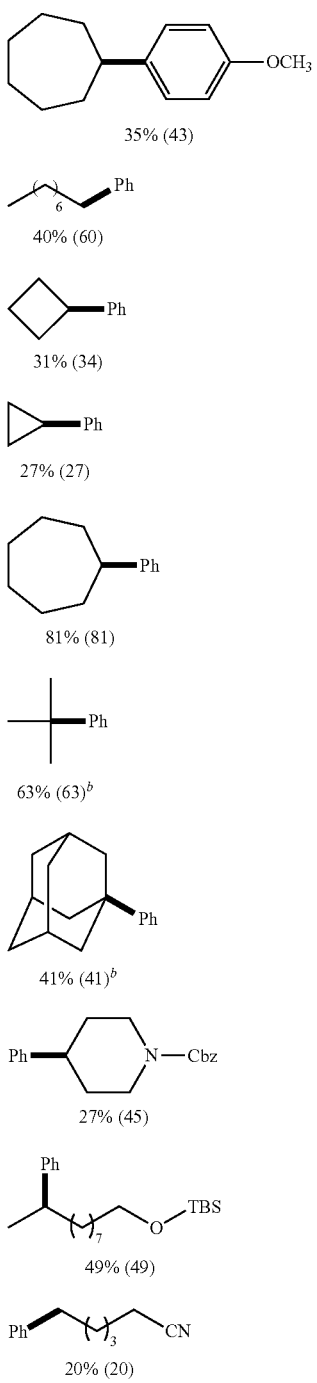

35% (43)

40% (60)

31% (34)

27% (27)

81% (81)

63% (63)[b]

41% (41)[b]

27% (45)

49% (49)

20% (20)

In conclusion, an air-stable iron(III)-based catalyst precursor for the Suzuki-Miyaura cross-coupling between alkyl halides and aryl boronic esters was developed, and a protocol for carrying out cross-coupling reactions without the aid of a glovebox was established. Bearing one β-diketiminate ligand and two acetylacetonate ligands, the new iron complex displayed longterm stability in the solid state, as assessed by a combination of $^1$H NMR spectroscopy, Mössbauer spectroscopy, and its sustained catalytic activity after being exposed to air for months. We anticipate that this advance will enable the practical implementation of iron-based catalysts for the Suzuki-Miyaura cross-coupling reaction. Considering that the reaction is particularly effective at incorporating alkyl halide substrates and it is compatible with heterocycles commonly observed in pharmaceuticals, we expect that iron-based complexes will. provide complementary reactivity to well-established palladium based catalysts used for the Suzuki-Miyaura cross-coupling of two sp2-hybridized substrates. The low toxicity of iron compared to nickel may also make these catalysts advantageous compared to air-stable nickel-based complexes that have previously been developed for similar reactions.[7-9] Ultimately, we hope that this improved protocol for iron-catalyzed Suzuki-Miyaura cross-coupling reactions paves the way for facile access to previously inaccessible structures that may be useful for structure-activity relationship studies in the pharmaceutical industry.

In an embodiment, the present invention provides for an iron(III) catalyst for Suzuki-Miyaura cross-coupling reactions, wherein the catalyst has a composition according to Formula 1:

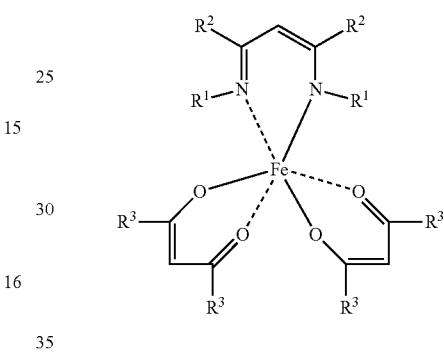

wherein each $R^1$ is independently selected from the group consisting of H, an alkyl group having 1 to 5 carbon atoms or phenyl and an alkyl substituted aryl group wherein the alkyl group has 1 to 5 carbon atoms; wherein each $R^2$ is independently selected from the group consisting of an alkyl group having 1 to 5 carbon atoms, phenyl, and an alkyl substituted aryl group wherein the alkyl group has 1 to 5 carbon atom; and each $R^3$ is independently selected from the group consisting of an alkyl group having 1 to 5 carbon atoms, phenyl, and an alkyl substituted aryl wherein the alkyl group has 1 to 5 carbon atoms. In such embodiments, the alkyl group is selected from the group consisting of methyl, ethyl, propyl, butyl, pentyl, isopropyl, neopentyl, tert-butyl, cyclopentyl, cyclopropyl, and $CF_3$. Further in such embodiments, the alkyl substituted aryl group is selected from the group consisting of 2,6-dialkyl, 3,5-dialkyl, and 2,4,6-trialkyl substituted aryl groups, and 2,4,6-trisubstituted aryl groups. For the dialkyl and trialkyl substituted aryl groups, the alkyl group is selected from the group consisting of methyl, ethyl, propyl, butyl, pentyl, isopropyl, neopentyl, tert-butyl, cyclopentyl, cyclopropyl, and $CF_3$. For the 2,4,6-trisubstituted aryl groups, substituents include 2,6-dialkyl substituents and a 4-substituent containing a halogen, an alkyl ether, and a dialkyl amine wherein the alkyl group is selected from the group consisting of methyl, ethyl, propyl, butyl, pentyl, isopropyl, neopentyl, tert-butyl, cyclopentyl, cyclopropyl, and $CF_3$. In one such embodiment, Formula 1 corresponds to:

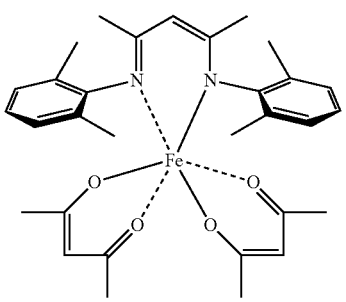

In another such embodiment, the iron(III) catalyst of formula 1 is stable in a solid state for a period of time selected from three to six months; three to nine months, six to nine months, each when stored in a desiccator.

In some embodiments, the iron(III) catalyst of formula 1 is air-stable. In some embodiments, the iron(III) catalyst of formula 1 is moisture-stable or water-stable. In some embodiments, the iron(III) catalyst of formula 1 can be stored for one, two, three, four, five, six, seven, eight, nine, ten, eleven or twelve months without losing its catalytic activity. In some embodiments, the iron(III) catalyst of formula 1 can be stored for one, two, three, four, or five, years without losing its catalytic activity.

In some embodiments, the iron(III) catalyst of formula 1 is used in Suzuki-Miyaura cross-coupling without a glovebox.

In another embodiment, the present disclosure provides for a making an iron(III) catalyst for Suzuki-Miyaura cross-coupling reactions. The method includes the steps of: (a) preparing a solution of an $Fe(acac)_3$ complex; (b) reacting a β-diketimine compound with butyllithium to form a β-diketiminate; and (c) mixing the β-diketiminate and the solution of an $Fe(acac)_3$ complex to form the iron(III) catalyst having a composition according to Formula 1. In one such embodiment, the β-diketimine compound is 2,4-bis[(2,6-dimethylphenyl)imino]pentane.

In some embodiments, the cross coupling reaction is a Suzuki-Miyaura cross coupling reaction. In some embodiments, the catalyst described herein may be employed at a ppm level, such as 1,000 ppm, 500 ppm, 300 ppm, 200 ppm, 100 ppm or less. In some embodiments, the catalyst described herein may be employed at a ppm level of about 50,000 ppm, about 40,000 ppm, about 30,000 ppm, about 20,000 ppm, about 10,000 ppm, about 9,000 ppm, about 8,000 ppm, about 7,000 ppm, about 6,000 ppm, about 5,000 ppm, about 4,000 ppm, about 3,000 ppm, about 2,000 ppm, about 1,000 ppm, or about 500 ppm.

In yet another embodiment, the present invention provides for a method of catalyzing Suzuki-Miyaura cross-coupling reaction, comprising contacting a compound A of formula $R^A$—X and a compound B of formula $R^B$-G with the iron(III) catalyst having a composition according to Formula 1, wherein $R^A$ is an alkyl group; X is halogen or sulfonate ester of the for OSO2R (R=tolyl, Me, $CF_3$; $R^B$ is an aryl and G is —$B(OH)_2$ or esters thereof. In such embodiments, $R^A$—X may be any alkyl halide/pseudohalide, wherein $R^A$ includes $CH_3$, primary, secondary, and tertiary alkyl and X is Br or I. In another such embodiment, $R^A$ is a secondary alkyl selected from the group consisting of isopropyl, 2-butyl, cyclopentyl, and cyclopropyl. In one such embodiment, $R^A$ is a tertiary alkyl selected from the group consisting of t-butyl and 2-(2-methyl)-butyl. Further in such embodiments, $R^B$-G (the boronic ester) can include any substituted aryl (unsubstituted, ortho substituted, meta substituted, and parasubstituted) boronic ester or heteroaryl boronic ester. Examples of $R^B$-G as heteroaryl boronic esters include indoles, pyridines, thiophenes, furans, and pyrizines. In such embodiments, $R^B$-G is selected from the group consisting of 2-thiophenyl boronic acid pinacol ester, 3-thiophenyl boronic acid pinacol ester, (3-(trifluoromethyl)phenyl) boronic acid pinacol ester, 3-furyl boronic acid pinacol ester, 6-quinolyl boronic acid pinacol ester, 6-(4-Boc-piperazin-1-yl)pyridine-3-boronic acid pinacol ester, (4-methoxyphenyl) boronic acid pinacol ester, and phenyl boronic acid pinacol ester. $R^B$-G may also be an alkyl borane of the structure R3B wherein the alkyl group may include $CH_3$, primary, secondary, and tertiary alkyl groups. In one such embodiment, $R^B$ is phenyl, 2-pyridinyl, 3-pyridinyl, or 4-pyridinyl.

In some embodiments, the catalyst described herein may be employed at a mole percent of either $R^A$—X or $R^B$-G, such as about 30%, about 25%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.9%, about 0.8%, about 0.7%, about 0.6%, about 0.5%, about 0.4%, about 0.3%, about 0.2%, about 0.1%, about 0.05%, about 0.01%, about 0.005%, or about 0.001%.

In some embodiments, the catalyst described herein may be employed at a range of mole percent of either $R^A$—X or $R^B$-G, such as between about 30% and about 0.001%, between about 25% and about 0.01%, between about 20% and about 0.05%, between about 15% and about 0.1%, between about 10% and about 0.5%, between about 8% and about 1%, between about 5% and about 0.1%, or between about 5% and about 0.01%.

Figure 2A:
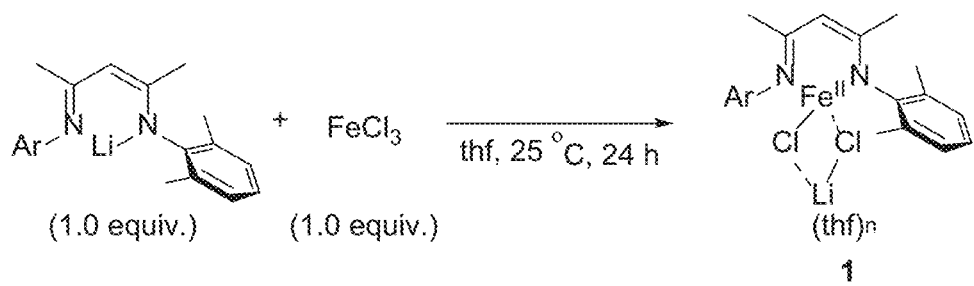
FIG. 2a illustrates a synthesis of an iron(III) complex supported by a β-diketiminate ligand through the addition of FeCl$_3$.
Figure 2B:
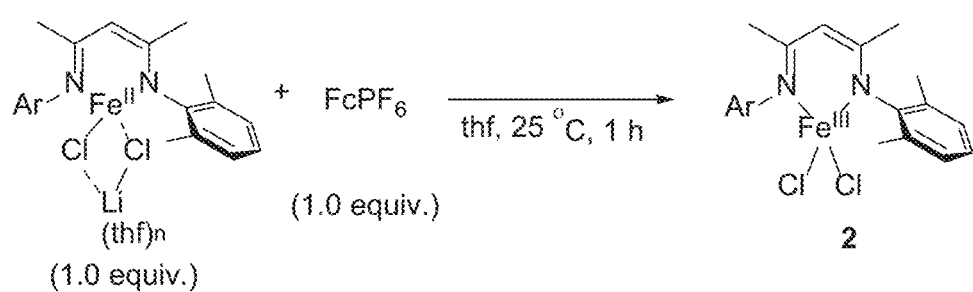
FIG. 2b illustrates a synthesis of a neutral iron(III) dichloride complex supported by a β-diketiminate ligand by the oxidation of the analogous iron (II) complex.

Reports for the design of iron-based complexes supported by β-diketiminate ligands proved the complexes effective for catalyzing Suzuki-Miyaura cross-coupling reactions.[19] Attempts to synthesize the analogous iron(III) complex by using the iron(III) salt $FeCl_3$ in place of $FeCl_2$, showed by $^1H$ NMR spectroscopy that the resulting product was identical to that of the previously used iron(II) complex 1, suggesting that the iron species is reduced in situ, as illustrated in FIG. 2a. FIG. 2b illustrates a synthesis approach to oxidize the iron(II) complex with the addition of an external oxidant, ferrocenium hexafluorophosphate.

Figure 3A:
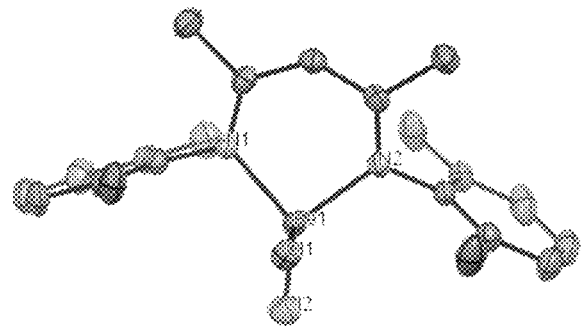
FIG. 3a illustrates the X-ray crystal structure of complex 2 with selected bond metrics.

X-ray crystallographic characterization of the resultant complex 2 confirmed the formation of a monomeric, neutral iron(III) dichloride complex 2, illustrated in FIG. 3a, which was active for the catalytic Suzuki-Miyaura cross-coupling of bromocycloheptane and phenyl boronic acid pinacol ester, delivering the product in 60% yield. While complex 2 displayed no change in its $^1H$ NMR spectrum immediately following exposure to air, no paramagnetic resonances were observed 24 hours after initial exposure to air, suggesting catalyst deactivation occurred.

Figure 2C:
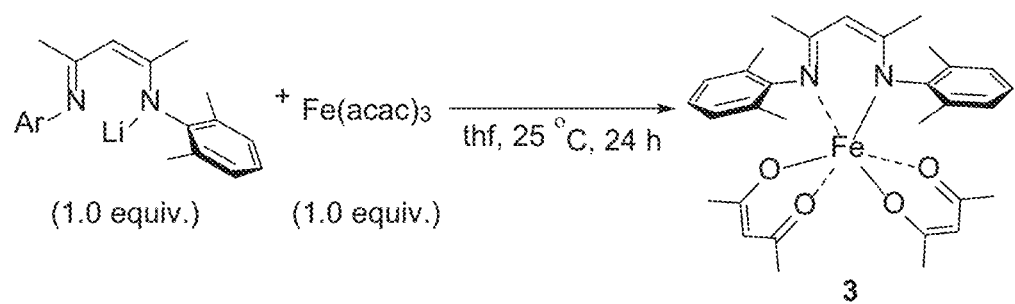
FIG. 2c illustrates the synthesis of an air-stable iron(III) catalyst complex supported by a β-diketiminate ligand and two acetylacetonate ("acac") ligands.
Figure 3B:
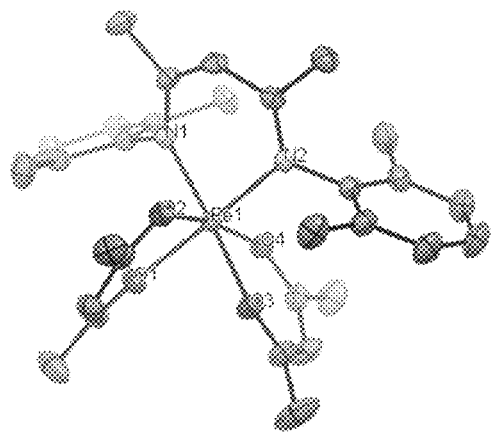
FIG. 3b illustrates the X-ray crystal structure of complex 3 with selected bond metrics. Thermal ellipsoids are drawn at the 50% probability level; hydrogen atoms are omitted for clarity.

As illustrated in FIG. 2c for an embodiment of the present invention, addition of the β-diketiminate ligand to the iron (III) salt $Fe(acac)_3$ resulted in the formation of a dark green iron(III) catalyst complex 3, which delivered the phenylcycloheptane cross-coupling product in 64% yield. Furthermore, iron(III) catalyst complex 3 demonstrated comparable catalytic activity and remained stable, as determined by $^1H$ NMR spectroscopy, in the solid-state up to six months following its storage in a benchtop desiccator exposed to air. X-ray crystallographic characterization of iron(III) catalyst complex 3 confirmed the formation of an octahedral iron complex supported by one β-diketiminate ligand and two acetylacetonate ligands as illustrated in FIG. 3b.

Figure 4B:
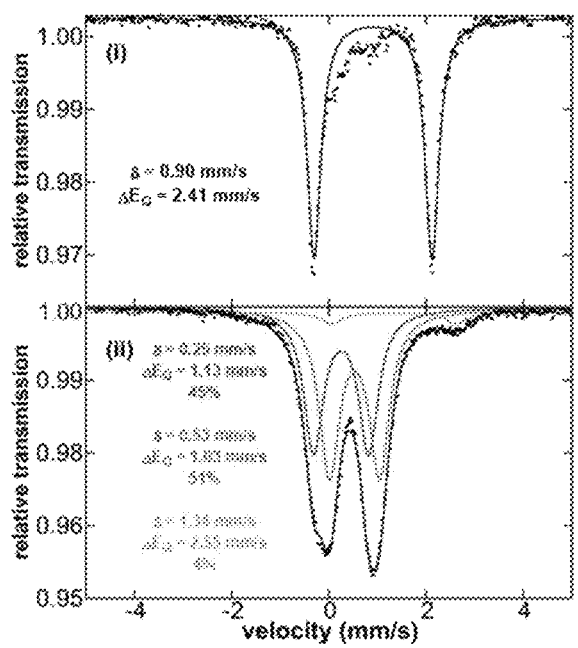
FIG. 4b illustrates a comparison of the 80 K $^{57}$Fe Mössbauer spectra of the previously synthesized iron (II)-based cross-coupling 1 i) prior to and ii) following exposure to air.
Figure 5:
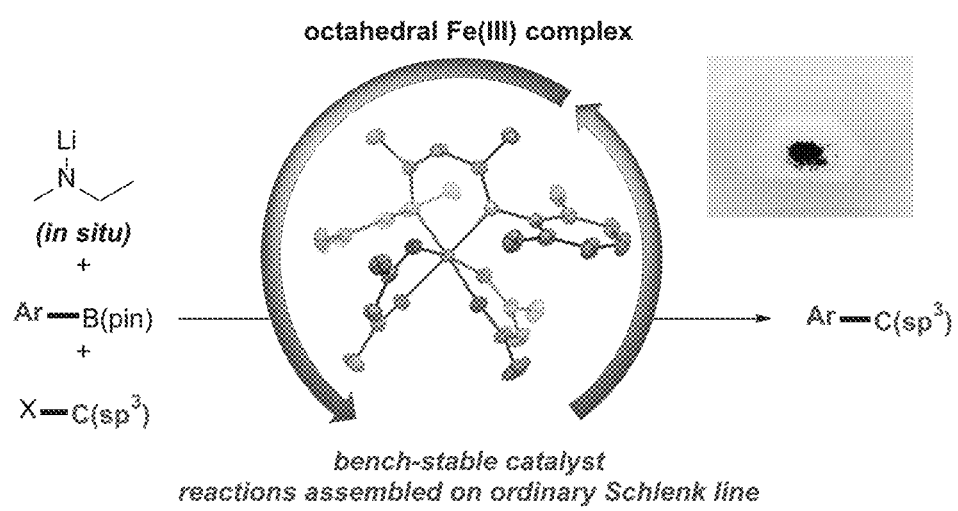
FIG. 5 schematically illustrates the Fe(III) catalyst disclosed herein.
Figure 6:
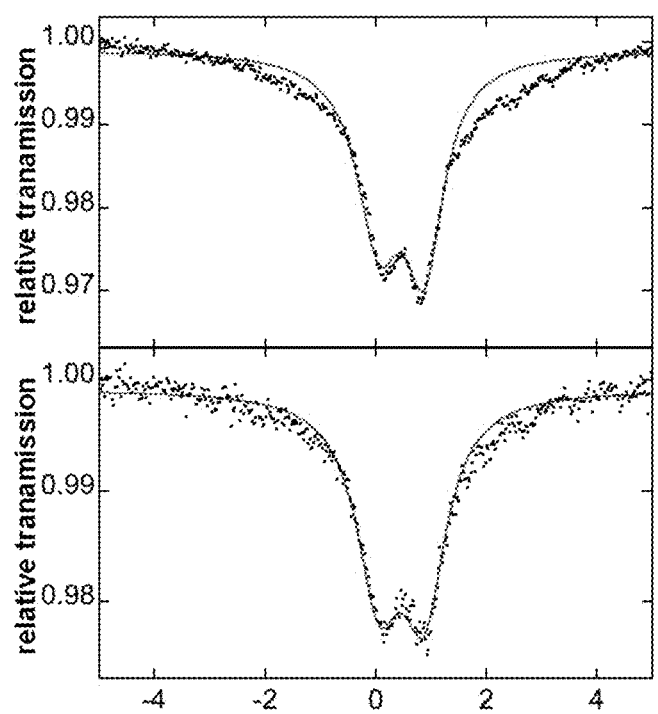
FIG. 6 illustrates comparison of the 80 K $^{57}$Fe Mössbauer spectra of compound 3, i) prior to and ii) following exposure to air for four months. Raw data for each spectrum are shown in black and the fit for the spectra are shown in red. While some slight peak asymmetry differences exist, both samples fit to the same parameters of δ=0.47 mm/s and $|\Delta E_Q|$=0.82 mm/s.

Effective magnetic moments measured in the solution-state for complex 2 and iron(III) catalyst complex 3 support the assignment of the iron(III) oxidation state ($\mu_{eff}$=6.54 and 7.04 for complexes 2 and 3, respectively). The speciation of the iron centers was also examined using $^{57}$Fe Mössbauer spectroscopy. The 80 K $^{57}$Fe Mössbauer spectrum of iron (III) complex 3 features a broad signal with δ=0.48 mm/s and $\Delta E_Q$=0.74 mm/s is consistent with a high-spin iron (III) species (FIG. 4a). Similar broadening has been previously observed in high spin iron (III) complexes.[20,21] Most importantly, the spectrum of a sample of iron(III) catalyst complex 3 after four months of continued exposure to air displayed no observable changes (by Mössbauer spectroscopy) from that of a freshly synthesized sample of the same complex. This experiment supported our hypothesis that higher oxidation state iron species are less prone to decomposition on the benchtop. A similar analysis of the iron(II) complex 1 before displayed marked differences in the Mössbauer spectra after exposure to air for only one hour, which suggested that the iron(II) catalyst precursor underwent near-complete conversion to a mixture of species. Additionally, significant changes were observed visually and in the $^1$H NMR spectrum of complex 1, which further confirmed that the complex underwent decomposition when exposed to air (FIG. 4b).

EXAMPLES

The present teachings, having been generally described, will be more readily understood by reference to the following examples, which are included merely for the purposes of illustration of certain aspects and embodiments of the present teachings, and are not intended to limit the scope of these teachings.

Experimental

Unless stated otherwise, all reactions were carried out in oven-dried glassware in a nitrogen-filled glovebox or using standard Schlenk line techniques. Solvents including tetrahydrofuran, pentane, and benzene were used after passage through two activated alumina columns under a blanket of argon and then degassed by brief exposure to vacuum. Deuterated solvents were dried over a sodium/benzophenone pot. Boronic acid pinacol esters were used after passage through alumina under a nitrogen atmosphere. Methylethylamine was purchased from TCI America; diethylamine was purchased from Sigma-Aldrich. Amines that were liquids at room temperature were dried over calcium hydride for at least 24 hours and then distilled under vacuum. Lithium amides were passed through a 250 micron sieve to ensure homogenous particle size prior to use. The lithium amide salts are pyrophoric when exposed to air, but their flammability is mitigated when they are dissolved in solution. The β-diketiminate ligand used for the synthesis of iron complexes 1 and 3 was synthesized as described previously.[31] Aryl boronic ester precursors for compounds 5, 8, and 9 were graciously provided by Amgen. Iron (III) chloride was purchased from Sigma-Aldrich and used without further purification. Iron (III) tris(acetoacetone) was purchased from Acros Organics and used without further purification. Alkyl halides were dried over calcium hydride for at least 24 hours and then distilled under vacuum.

Nuclear magnetic resonance (NMR) spectra were recorded at ambient temperature on Varian vNMRs operating at 400 MHZ, 500 MHz, or 600 MHz for $^1$H NMR, at 160 MHz for $^{11}$B NMR, and at 125 MHz for $\{^1H\}^{13}$C NMR. Spectra were referenced using shifts corresponding to solvent residual protic impurities. Boron trifluoride diethyl etherate (BF$_3$·Et$_2$O) was used as an external standard for $^{11}$B NMR (0.0 ppm). The line listing for NMR spectra of diamagnetic compounds are reported as follows: chemical shift (multiplicity, coupling constant, integration); paramagnetic compounds are reported as follows: chemical shift (peak width at half height, number of protons). All paramagnetic spectra were collected at 25° C. Solvent suppressed spectra were collected for paramagnetic complexes in THF using the PRESAT macro on the vNMR software. Infrared spectra were recorded on a Bruker Alpha attenuated total reflectance infrared spectrometer. High resolution mass spectra were obtained at the Boston College Mass Spectrometry Facility on a JEOL AccuTOF DART instrument. Single crystal X-ray Intensity data were measured on a Bruker Kappa Apex Duo diffractometer using a high brightness IS copper source with multi-layer mirrors. The low temperature device used is an Oxford 700 series Cryostream system with temperature range of 80-400 K. An Olympus SZ1145 stereo zoom microscope was used to view and mount crystals. The crystal structure was solved using ShellX. Solution state magnetic moments were obtained following the method described by Evans.[42] For Mössbauer spectroscopy, solid samples were prepared under an inert atmosphere within a glovebox with a liquid nitrogen fill port to freeze-trap solid samples at 77 K. Samples were loaded into Delrin sample cups and then frozen in liquid nitrogen. Low temperature $^{57}$Fe Mössbauer measurements were performed using a Janis SVT-400T N$_2$ cryostat for analysis at 80 K. Isomer shift values were measured relative to an α-Fe standard at 298 K. All of the Mössbauer spectra were fit using WMoss (See Co.) software. The associated parameter errors in the fit analyses include the following: δ±0.02 mm/s, $\Delta E_Q$±3%. The multicomponent fit analyses have an associated quantitation error of ±3%. Since only zero-field Mössbauer measurements were performed, all quadrupole splitting parameters reported herein are absolute values.

Example 1: General Procedure for the Iron-Catalyzed Cross-Coupling Reaction of Aryl Boronic Esters and Alkyl Halides Performed in a Glovebox In a nitrogen-filled glovebox, iron complex 3 (0.025 mmol, 10 mol %, 14 mg) and lithium ethylmethyl amide (0.5 mmol, 2.0 equiv., 32 mg) were added to a 7 mL scintillation vial containing a magnetic stir bar. A 1 mL benzene solution of boronic acid pinacol ester (0.5 mmol, 2.0 equiv.) and alkyl halide (0.25 mmol, 1.0 equiv.) was added to the stirring vial, followed immediately by benzene (5 mL) and sealing of the reaction vessel. The reaction mixture was allowed to stir vigorously and quickly became homogenous. After 24 hours of stirring, the reaction was quenched with a saturated aqueous solution of ammonium chloride (10 mL). The aqueous phase was washed with dichloromethane (3×40 mL) and the combined organic phases were dried over sodium sulfate and filtered through celite. Trimethoxybenzene (42 mg, 0.25 mmol) was added as an internal standard before evaporating the solvent in vacuo. A spectroscopic yield was determined by $^1$H NMR spectroscopy before the crude product was purified by silica flash column chromatography to give isolated yields.

Example 2: General Procedure for the Iron-Catalyzed Cross-Coupling Reaction of Aryl Boronic Esters and Alkyl Halides Under Nitrogen on a Schlenk Line On the Schlenk line, to an oven-dried 10 mL Schlenk tube equipped with stir bar and purged with $N_2$ was added ethylmethyl amine (0.55 mmol, 2.1 equiv., 31 mg, 45 µL) and anisole (0.5 mL). A solution of n-butyllithium in hexanes (2.5 M, 0.5 mmol, 2.0 equiv.) was added to the reaction vessel, whereupon the reaction mixture turned cloudy. The reaction mixture was allowed to stir at ambient temperature for 15 minutes. Iron complex 3 (0.025 mmol, 10 mol %) was weighed into a round-bottom flask open to air, which was evacuated on the Schlenk line and backfilled with nitrogen. The iron complex was dissolved in benzene (1 mL) and then added simultaneously to the Schlenk tube by syringe with a 1 mL benzene solution of boronic acid pinacol ester (0.5 mmol, 2.0 equiv.) and alkyl halide (0.25 mmol, 1.0 equiv.) prepared in a separate syringe. The reaction mixture was diluted to a volume of 7 mL with benzene, then allowed to stir at room temperature under a nitrogen atmosphere. After 24 hours, the reaction was quenched with a saturated aqueous solution of ammonium chloride (10 mL). The aqueous phase was washed with dichloromethane (3×40 mL) and the combined organic phases were dried over sodium sulfate and filtered through celite. Trimethoxybenzene (42 mg, 0.25 mmol) was added as an internal standard before evaporating the solvent in vacuo. A spectroscopic yield was determined by $^1$H NMR spectroscopy before the crude product was purified by silica flash column chromatography to give isolated yields.

Example 3: Synthesis of 2,4-bis[(2,6-dimethylphenyl)imino]pentane Iron Chloride Complex (1)

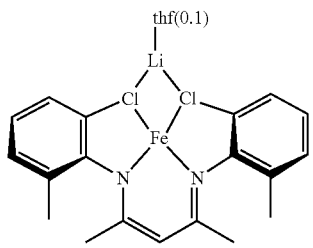

To an oven-dried 50 mL round-bottom flask equipped with stirbar was added 2,4-bis[(2,6-dimethylphenyl)imino]pentane (500 mg, 1.63 mmol, 1.0 equiv.) and pentane (25 mL). On the Schlenk line, the mixture was cooled to −78° C. and degassed by placing the solution under vacuum for at least 5 minutes. A solution of butyl lithium in hexanes (0.9 mL, 1.8 M, 1.63 mmol) was added dropwise while stirring. A pale yellow precipitate forms upon warming to ambient temperature. The reaction mixture was warmed to room temperature while stirring before the solvent was removed under vacuum. The sealed reaction vessel was transferred into a glovebox, where the solid was collected on a frit and washed with cold pentane (5 mL at −40° C.). The solid was dried and weighed to determine stoichiometry for the next step. No characterization of the lithium salts of the ligand were carried out. The collected deprotonated ligand (500 mg, 1.6 mmol, 1.0 equiv.) was then dissolved in THF (10 mL) in a 20 mL scintillation vial. This solution was added dropwise to a slurry of iron trichloride (260 mg, 1.6 mmol, 1.0 equiv.) in THF (10 mL) prepared in a separate scintillation vial equipped with stir bar. This mixture was allowed to stir for 1 hour before being placed in a −40° C. refrigerator overnight to precipitate. The reaction mixture was filtered through celite and washed with THF, then the filtrate concentrated in vacuo. The residue was washed with cold pentane (10 mL), dried, and collected as a dark yellow solid (450 mg, 45%). Spectral data matched that of the analogous iron (II) dihalide complex. $^1$H NMR (400 MHz, THF) δ −68.7 ($w_{1/2}$=180 Hz, 6H), −52.0 ($w_{1/2}$=100 Hz, 2H), −39.7 ($w_{1/2}$=264 Hz, 1H), 6.2 ($w_{1/2}$=254 Hz, 12H), 16.1 ($w_{1/2}$=82 Hz, 4H) ppm.[31]

Example 4: Synthesis of 2,4-bis[(2,6-dimethylphenyl)imino]pentane Iron (III) Dichloride (2)

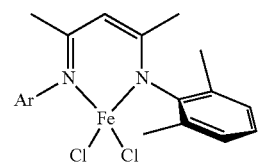

In a nitrogen-filled glovebox, to a 7 mL scintillation vial equipped with stir bar was added 2,4-bis[(2,6-dimethylphenyl)imino]pentane iron (II) chloride complex (100 mg, 0.17 mmol, 1.0 equiv.) and ferrocenium hexafluorophosphate (57 mg, 0.17 mmol, 1.0 equiv.). The solids were dissolved in THF (2 mL), at which point the reaction mixture turned a dark purple immediately. The reaction mixture was allowed to stir for 1 hour at ambient temperature, then the solvent evaporated in vacuo. The crude material was subjected to recrystallization from pentane at −40° C. overnight to afford the title compound as a dark purple solid of X-ray quality (25 mg, 66% yield). $^1$H NMR (400 MHZ, THF, solvent suppressed) δ 68.64 ($w_{1/2}$=1007 Hz, 12H), 16.12 ($w_{1/2}$=224 Hz, 2H), −36.25 ($w_{1/2}$=800 Hz, 4H), −52.01 ($w_{1/2}$=248 Hz, 1H), −68.68 ($w_{1/2}$=335 Hz, 6H). IR: 3357, 1560, 1523, 1473, 1446, 1276, 1193, 843, 773, 555 cm$^{-1}$. $\mu_{eff}$(THF, 25° C.): 6.54 $\mu_B$. HRMS-DART (m/z): [M+H]$^+$ calculated for $C_{21}H_{26}N_2Cl_2Fe$, 432.19. found, 432.08.

Example 5: Synthesis of 2,4-bis[(2,6-dimethylphenyl)imino]pentane Iron (III) bis(acetylacetone) (3)

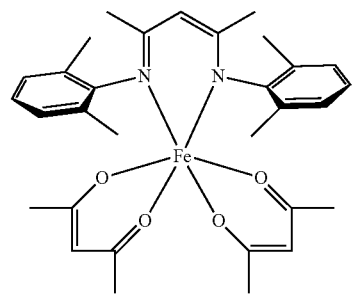

To an oven-dried 100 mL pear-shaped round-bottom flask equipped with stir bar was added 2,4-bis[(2,6-dimethylphenyl)imino]pentane ligand (4.59 g, 14.97 mmol, 1.05 equiv.) and pentane (25 mL). A 180° joint with stopcock was attached and the apparatus was sealed with a rubberband and copper wire. On the Schlenk line, the mixture was cooled to −78° C. and degassed by placing the solution under vacuum for 5 minutes. A solution of butyllithium in hexanes (4.75 mL, 3 M, 1 equiv.) was added dropwise via sidearm while stirring at −78° C. A pale yellow precipitate forms upon warming to ambient temperature. The reaction mixture was allowed to stir 30 minutes at ambient temperature before the solvent was removed under vacuum. The sealed reaction apparatus was transferred to a glovebox, and the solid was collected on a frit and washed with cold pentane (10 mL). The collected solid was dried and weighed to determine stoichiometry for the next step. The deprotonated ligand (4.56 g, 14.6 mmol, 1 equiv.) was dissolved in THF (5 mL) in a 20 mL scintillation vial. This solution was added dropwise to a suspension of Fe(acac)$_3$ (5.16 g, 14.6 mmol, 1 equiv.) in THF (5 mL) prepared in a separate scintillation vial equipped with stir bar. This mixture was allowed to stir overnight, during which time it turned from red-orange to dark green. The reaction mixture was cooled before being passed through celite, then washed with additional THF (~20 mL) before it was concentrated under vacuum. The resulting solid residue was washed with pentane, dried, and collected to afford the product as a dark green solid (4.9 g, 60% yield). $^1$H NMR (500 MHZ, C$_6$D$_6$) δ 42.94 (w$_{1/2}$=1550 Hz, 4H), 33.09 (w$_{1/2}$=4136 Hz, 6H), 20.19 (w$_{1/2}$=1827 Hz, 12H), 15.83 (w$_{1/2}$=1568 Hz, 8H), −31.79 (w$_{1/2}$=425 Hz, 3H), −47.02 (w$_{1/2}$=1410 Hz, 6H). IR: 2919, 1577, 1520, 1371, 1272, 1020, 764 cm$^{-1}$. $\mu_{eff}$ (THF, 25° C.): 7.04 $\mu_B$. HRMS-DART (m/z): [M+H]$^+$ calculated for C$_{31}$H$_{39}$N$_2$O$_4$Fe, 559.51. found, 560.23. Elemental analysis for C$_{31}$H$_{39}$N$_2$O$_4$Fe: calculated C, 66.55% H, 7.03% N, 5.01%. found C, 63.17% H, 6.65% N, 4.52%. Discrepancies in the elemental analysis are believed to be due to the presence of residual Fe(acac)$_3$.

Example 6: Synthesis of 2-Cycloheptyl Thiophene (4)

Compound 4 was synthesized from bromocycloheptane and 2-thiophenyl boronic acid pinacol ester according to the general procedure on the Schlenk line, using catalyst 3 and purified by silica gel flash column chromatography, eluting with 100% hexanes to afford the product as a colorless oil (13 mg, 32% spectroscopic yield, 38% based on recovered starting material, 29% isolated). R$_f$=0.75 (100% hexanes). $^1$H NMR (400 MHZ, CDCl$_3$): δ 7.07 (d, J=5.1, 1H), 6.90 (t, J=5.1, 3.4 Hz, 1H), 6.78 (d, 1H), 3.04 (septet, J=4.6 Hz, 1H), 2.12-2.03 (m, 1H), 1.81-1.64 (m, 4H), 1.57-1.48 (m, 5H) ppm. NMR spectrum is in agreement with literature precedence.[31]

Example 7: Synthesis of 3-Cycloheptyl Thiophene (5)

Compound 5 was synthesized from bromocycloheptane and 3-thiophenyl boronic acid pinacol ester according to the general procedures in the glovebox and on the Schlenk line, using catalyst 3 and purified by silica gel flash column chromatography, eluting with 100% hexanes to afford the product as a colorless oil (23 mg, 53% spectroscopic yield, 58% based on recovered starting material, 51% isolated). R$_f$=0.75 (100% hexanes). $^1$H NMR (400 MHZ, CDCl$_3$): δ 7.22 (dd, J=5.0, 3.0 Hz, 1H), 6.97 (d, J=5.0 Hz, 1H), 6.91 (s, 1H), 2.82 (septet, J=9.9, 4.7 Hz, 1H), 1.98 (m, 2H), 1.80-1.72 (m, 2H), 1.71-1.47 (m, 8H) ppm. NMR spectrum is in agreement with literature precedence.[31]

Example 8: Synthesis of (3-(trifluoromethyl)phenyl) cycloheptane (6)

Compound 6 was synthesized from bromocycloheptane and (3-(trifluoromethyl)phenyl) boronic acid pinacol ester according to the general procedure on the Schlenk line, using catalyst 3 and purified by silica gel flash column chromatography, eluting with 100% hexanes to afford the product as a colorless oil (41 mg, 66% spectroscopic yield, 66% based on recovered starting material, 68% isolated). R$_f$=0.80 (100% hexanes). $^1$H NMR (400 MHZ, CDCl$_3$): δ 7.43-7.36 (m, 4H), 2.73 (septet, 1H), 1.95-1.86 (m, 2H), 1.86-1.77 (m, 2H), 1.74-1.51 (m, 8H) ppm. NMR spectrum is in agreement with literature precedence.[22]

Example 9: Synthesis of 3-Cycloheptyl Furan (7)

Compound 7 was synthesized from bromocycloheptane and 3-furyl boronic acid pinacol ester according to the general procedure on the Schlenk line, using catalyst 3 and purified by silica gel flash column chromatography, eluting with 100% hexanes to afford the product as a colorless oil (23 mg, 55% spectroscopic yield, 60% based on recovered starting material, 56% isolated). R$_f$=0.95 (100% hexanes). $^1$H NMR (400 MHZ, CDCl$_3$): δ 7.33 (s, 1H), 7.19 (s, 1H), 6.28 (s, 1H), 2.63 (septet, 1H), 1.94 (m, 2H), 1.76-1.62 (m, 4H), 1.57-1.48 (m, 6H) ppm. NMR spectrum is in agreement with literature precedence.[31]

Example 10: Synthesis of 6-Cycloheptyl Quinoline (8)

Compound 8 was synthesized from bromocycloheptane and 6-quinolyl boronic acid pinacol ester according to the general procedure on the Schlenk line heated to 50° C., using catalyst 3 and purified by silica gel flash column chromatography, eluting with 100% hexanes to afford the product as a colorless oil (20 mg, 34% spectroscopic yield, 45% based on recovered starting material, 36% isolated). R$_f$=0.45 (30% ethyl acetate in hexanes). $^1$H NMR (400 MHZ, CDCl$_3$): δ 8.85 (d, J=4.1 Hz, 1H), 8.13 (d, J=8.3 Hz, 1H), 8.03 (d, J=8.6 Hz, 1H), 7.63-7.55 (m, 2H), 7.45-7.36 (m, 1H), 2.88i (septet, 1H), 2.04-1.95 (m, 2H), 1.89-1.79 (m, 2H), 1.79-1.71 (m, 4H), 1.71-1.57 (m, 4H) ppm. NMR spectrum is in agreement with literature precedence.[31]

Example 11: Synthesis of 6-(4-Boc-piperazin-1-yl)-3-cycloheptyl Pyridine (9)

Compound 9 was synthesized from bromocycloheptane and 6-(4-Boc-piperazin-1-yl)pyridine-3-boronic acid pinacol ester according to the general procedure on the Schlenk line heated to 50° C., using catalyst 3 and purified by silica gel flash column chromatography, eluting with 100% hexanes to afford the product as a colorless oil (65 mg, 72% spectroscopic yield, 72% based on recovered starting material, 72% isolated). R$_f$=0.45 (30% ethyl acetate in hexanes). 1H NMR (400 MHZ, CDCl$_3$): δ 8.04 (s, 1H), 7.37 (m, 1H), 6.59 (m, 1H), 3.53 (m, 4H), 3.46 (m, 4H), 2.59 (septet, 1H), 1.89-1.81 (m, 2H), 1.81-1.73 (m, 2H), 1.72-1.65 (m, 2H), 1.65-1.51 (m, 6H), 1.48 (s, 9H) ppm. NMR spectrum is in agreement with literature precedence.[31]

Example 12: Synthesis of (4-methoxyphenyl) cyclohexane (10)

Compound 10 was synthesized from bromocycloheptane and (4-methoxyphenyl) boronic acid pinacol ester according to the general procedure on the Schlenk line, using catalyst 3 and purified by silica gel flash column chromatography, eluting with 100% hexanes to afford the product as a white solid (18 mg, 34% spectroscopic yield, 43% based on recovered starting material, 35% isolated). $R_f$=0.60 (10% ethyl acetate in hexanes). $^1$H NMR (500 MHz, CDCl$_3$): δ 7.11 (d, J=8.4 Hz, 2H), 6.82 (d, J=8.4 Hz, 2H), 2.61 (septet, J=10.3, 5.1 Hz, 1H), 1.94-1.82 (m, 2H), 1.82-1.72 (m, 2H), 1.72-1.64 (m, 2H), 1.64-1.49 (m, 6H) ppm. NMR spectrum is in agreement with literature precedence.[22]

Example 13: Synthesis of Phenyloctane (11)

Compound 11 was synthesized from bromooctane and phenyl boronic acid pinacol ester according to the general procedure on the Schlenk line, using catalyst 3 and purified by silica gel flash column chromatography, eluting with 100% hexanes to afford the product as a colorless oil (19 mg, 39% spectroscopic yield, 60% based on recovered starting material, 40% isolated). $R_f$=0.60 (100% hexanes). $^1$H NMR (400 MHZ, CDCl$_3$): δ 7.27 (m, 2H), 7.18 (d, J=7.2 Hz, 3H), 2.60 (t, J=7.5 Hz, 2H), 1.65-1.57 (m, 2H), 1.32-1.26 (m, 10H), 0.90-0.86 (m, 3H) ppm. NMR spectrum is in agreement with literature precedence.[31]

Example 14: Synthesis of Phenylcyclobutane (12)

Compound 12 was synthesized from bromocyclobutane and phenyl boronic acid pinacol ester according to the general procedure on the Schlenk line, using catalyst 3 and purified by silica gel flash column chromatography, eluting with 100% hexanes to afford the product as a colorless oil (10 mg, 34% spectroscopic yield, 34% based on recovered starting material, 31% isolated). $R_f$=0.70 (100% hexanes). $^1$H NMR (400 MHZ, CDCl$_3$): δ 7.33-7.14 (m, 5H), 3.56 (p, J=8.8 Hz, 1H), 2.40-1.81 (m, 6H) ppm. NMR spectrum is in agreement with literature precedence.[31]

Example 15: Synthesis of Phenylcyclopropane (13)

Compound 13 was synthesized from bromocyclopropane and phenyl boronic acid pinacol ester according to the general procedure on the Schlenk line, using catalyst 3 and purified by silica gel flash column chromatography, eluting with 100% hexanes to afford the product as a colorless oil (8 mg, 27% spectroscopic yield, 27% based on recovered starting material, 27% isolated). $R_f$=0.75 (100% hexanes). $^1$H NMR (400 MHZ, CDCl$_3$) δ 7.47 (d, J=7.4 Hz, 2H), 7.14 (t, J=7.5 Hz, 1H), 7.09 (d, J=7.8 Hz, 2H), 1.91 (m, 1H), 0.97 (q, J=8.4 Hz, 2H), 0.71 (q, J=4.6 Hz, 2H) ppm. NMR spectrum is in agreement with literature precedence.[31]

Example 16: Synthesis of Phenylcycloheptane (14)

Compound 14 was synthesized from bromocycloheptane and phenyl boronic acid pinacol ester according to the general procedures in the glovebox and on the Schlenk line, using catalyst 3 and purified by silica gel flash column chromatography, eluting with 100% hexanes to afford the product as a colorless oil (13 mg, 32% spectroscopic yield, 38% based on recovered starting material, 29% isolated). $R_f$=0.60 (100% hexanes). $^1$H NMR (500 MHZ, CDCl$_3$): δ 7.23-7.33 (m, 2H), 7.08-7.23 (m, 2H), 2.66 (tt, J=10.7, 3.7 Hz, 1H), 1.92 (ddt, J=13.5, 6.6, 3.3 Hz, 2H), 1.80 (ddd, J=13.4, 6.6, 3.4 Hz, 2H), 1.46-1.78 (m, 8H) ppm. NMR spectrum is in agreement with literature precedence.[22]

Example 17: Synthesis of Tert-Butyl Benzene (15)

Compound 15 was synthesized from tert-butyl chloride and phenyl boronic acid pinacol ester according to the general procedure on the Schlenk line, using catalyst 3 and purified by silica gel flash column chromatography, eluting with 100% hexanes to afford the product as a colorless oil (21 mg, 63% isolated). $R_f$=0.60 (100% hexanes). $^1$H NMR (400 MHZ, CDCl$_3$) δ 7.84-7.78 (m, 2H), 7.48-7.42 (m, 1H), 7.37 (t, J=7.4 Hz, 2H), 1.35 (s, 9H) ppm. NMR spectrum is in agreement with literature precedence.[31]

Example 18: Synthesis of Adamantylbenzene (16)

Compound 16 was synthesized from chloroadamantane and phenyl boronic acid pinacol ester according to the general procedure on the Schlenk line, using catalyst 3 and purified by silica gel flash column chromatography, eluting with 100% hexanes to afford the product as a white solid (22 mg, 41% isolated). $R_f$=0.60 (100% hexanes). $^1$H NMR (500 MHz, CDCl$_3$): δ 7.2-7.4 (m, 5H), 2.10 (m, 3H), 1.92 (m, 6H), 1.77 (m, 6H) ppm. NMR spectrum is in agreement with literature precedence.[31]

Example 19: Synthesis of 4-phenylpiperidine-1-carboxylic Acid Benzyl Ester (17)

Compound 17 was synthesized from 4-bromopiperidine-1-carboxylic acid benzyl ester and phenyl boronic acid pinacol ester according to the general procedure on the Schlenk line, using catalyst 3 and purified by silica gel flash column chromatography, eluting with 100% hexanes to afford the product as a colorless oil (20 mg, 31% spectroscopic yield, 45% based on recovered starting material, 27% isolated). $R_f$=0.20 (15% ethyl acetate in hexanes). $^1$H NMR (500 MHz, CDCl$_3$): δ 7.40-7.26 (m, 7H), 7.23-7.17 (m, 3H), 5.16 (s, 2H), 4.34 (br s, 2H), 2.89 (m, 2H), 2.67 (tt, J=12.0, 3.2 Hz, 1H), 1.85 (d, J=13.2 Hz, 2H), 1.70-1.61 (m, 2H) ppm. NMR spectrum is in agreement with literature precedence.[31]

Example 20: Synthesis of tert-butyldimethyl((9-phenyldecyl)oxy)silane (18)

Compound 18 was synthesized from tert-butyldimethyl ((9-bromodecyl)oxy)silane and phenyl boronic acid pinacol ester according to the general procedure on the Schlenk line, using catalyst 3 and purified by silica gel flash column chromatography, eluting with 100% hexanes to afford the product as a colorless oil (43 mg, 48% spectroscopic yield, 48% based on recovered starting material, 49% isolated). $R_f$=0.15 (100% pentane). $^1$H NMR (500 MHZ, CDCl$_3$): δ 7.32-7.26 (m, 2H), 7.20-7.10 (m, 3H), 3.58 (m, 2H), 2.67 (q, J=7.1 Hz, 1H), 1.58-1.54 (m, 2H), 1.51-1.45 (m, 2H), 1.34-1.19 (m, 13H), 1.18-1.11 (m, 2H), 0.90 (s, 9H), 0.04 (s, 6H) ppm. NMR spectrum is in agreement with literature precedence.[31]

Example 21: Synthesis of 5-phenylpentyl Cyanide (19)

Compound 19 was synthesized from 5-bromopentyl cyanide and phenyl boronic acid pinacol ester according to the general procedure on the Schlenk line, using catalyst 3 and purified by silica gel flash column chromatography, eluting with 100% hexanes to afford the product as a colorless oil (9 mg, 18% spectroscopic yield, 18% based on recovered starting material, 20% isolated). $R_f$=0.15 (5% ethyl acetate in hexanes). $^1$H NMR (400 MHZ, CDCl$_3$): δ 7.28 (t, J=7.4 Hz, 2H), 7.20-7.14 (m, 3H), 2.62 (t, J=7.5 Hz, 2H), 2.33 (t, J=7.0 Hz, 2H), 1.74-1.51 (m, 4H), 1.56-1.43 (m, 2H) ppm. NMR spectrum is in agreement with literature precedence.[43]

REFERENCES (1) Miyaura, N.; Yamada, K.; Suzuki, A. A New Stereospecific Cross-Coupling by the Palladium-Catalyzed Reaction of 1-Alkenylboranes with 1-Alkenyl or 1-Alkynyl Halides. Tetrahedron Lett. 1979, 20 (36), 3437-3440. https://doi.org/10.1016/S0040-4039(01)95429-2.

(2) Brown, D. G.; Boström, J. Analysis of Past and Present Synthetic Methodologies on Medicinal Chemistry: Where Have All the New Reactions Gone? J. Med. Chem. 2016, 59 (10), 4443-4458. https://doi.org/10.1021/acs.jmedchem.5b01409.

(3) Choi, J.; Fu, G. C. Transition Metal-Catalyzed Alkyl-Alkyl Bond Formation: Another Dimension in Cross-Coupling Chemistry. Science (80-.). 2017, 356 (6334), eaaf7230. https://doi.org/10.1126/science.aaf7230.

(4) Han, F.-S. Transition-Metal-Catalyzed Suzuki-Miyaura Cross-Coupling Reactions: A Remarkable Advance from Palladium to Nickel Catalysts. Chem. Soc. Rev. 2013, 42 (12), 5270. https://doi.org/10.1039/c3cs35521g.

(5) Balcells, D.; Nova, A. Designing Pd and Ni Catalysts for Cross-Coupling Reactions by Minimizing Off-Cycle Species. ACS Catal. 2018, 8 (4), 3499-3515. https://doi.org/10.1021/acscatal.8b00230.

(6) Ananikov, V. P. Nickel: The "Spirited Horse" of Transition Metal Catalysis. ACS Catal. 2015, 5 (3), 1964-1971. https://doi.org/10.1021/acscatal.5b00072.

(7) Zhou, J.; Fu, G. C. Suzuki Cross-Couplings of Unactivated Secondary Alkyl Bromides and Iodides. J. Am. Chem. Soc. 2004, 126 (5), 1340-1341. https://doi.org/10.1021/ja039889k.

(8) Zultanski, S. L.; Fu, G. C. Nickel-Catalyzed Carbon-Carbon Bond-Forming Reactions of Unactivated Tertiary Alkyl Halides: Suzuki Arylations. J. Am. Chem. Soc. 2013, 135 (2), 624-627. https://doi.org/10.1021/ja311669p.

(9) González-Bobes, F.; Fu, G. C. Amino Alcohols as Ligands for Nickel-Catalyzed Suzuki Reactions of Unactivated Alkyl Halides, Including Secondary Alkyl Chlorides, with Arylboronic Acids. J. Am. Chem. Soc. 2006, 128 (16), 5360-5361. https://doi.org/10.1021/ja0613761.

(10) Kharasch, M. S.; Fields, E. K. Factors Determining the Course and Mechanisms of Grignard Reactions. IV. The Effect of Metallic Halides on the Reaction of Aryl Grignard Reagents and Organic Halides 1. J. Am. Chem. Soc. 1941, 63 (9), 2316-2320. https://doi.org/10.1021/ja01854a006.

(11) Tamura, M.; Kochi, J. K. Vinylation of Grignard Reagents. Catalysis by Iron. J. Am. Chem. Soc. 1971, 93 (6), 1487-1489. https://doi.org/10.1021/ja00735a030.

(12) Furstner, A.; Leitner, A.; Méndez, M.; Krause, H. Iron-Catalyzed Cross-Coupling Reactions. J. Am. Chem. Soc. 2002, 124 (46), 13856-13863. https://doi.org/10.1021/ja027190t.

(13) Egorova, K. S.; Ananikov, V. P. Toxicity of Metal Compounds: Knowledge and Myths. Organometallics 2017, 36 (21), 4071-4090. https://doi.org/10.1021/acs.organomet.7b00605.

(14) Cahiez, G.; Avedissian, H. Highly Stereo and Chemoselective Iron-Catalyzed Alkenylation of Organomagnesium Compounds. Synthesis (Stuttg). 1998, No. 8, 1199-1205. https://doi.org/10.1055/s-1998-2135.

(15) Fürstner, A.; Leitner, A. Iron-Catalyzed Cross-Coupling Reactions of Alkyl-Grignard Reagents with Aryl Chlorides, Tosylates, and Triflates. Angew. Chemie—Int. Ed. 2002, 41 (4), 609-612. https://doi.org/10.1002/1521-3773(20020215)41:4<609::AID-ANIE609>3.0.CO;2-M.

(16) Nakamura, M.; Matsuo, K.; Ito, S.; Nakamura, E. Iron-Catalyzed Cross-Coupling of Primary and Secondary Alkyl Halides with Aryl Grignard Reagents. J. Am. Chem. Soc. 2004, 126 (12), 3686-3687. https://doi.org/10.1021/ja049744t.

(17) Bisz, E.; Szostak, M. Iron-Catalyzed C(Sp2)-C(Sp3) Cross-Coupling of Chlorobenzenesulfonamides with Alkyl Grignard Reagents: Entry to Alkylated Aromatics. J. Org. Chem. 2019, 84 (3), 1640-1646. https://doi.org/10.1021/acs.joc.8b02886.

(18) Lo, J. C.; Yabe, Y.; Baran, P. S. A Practical and Catalytic Reductive Olefin Coupling. J. Am. Chem. Soc. 2014, 136 (4), 1304-1307. https://doi.org/10.1021/ja4117632.

(19) Lo, J. C.; Gui, J.; Yabe, Y.; Pan, C.-M.; Baran, P. S. Functionalized Olefin Cross-Coupling to Construct Carbon-Carbon Bonds. Nature 2014, 516 (7531), 343-348. https://doi.org/10.1038/nature14006.

(20) Lo, J. C.; Kim, D.; Pan, C.-M.; Edwards, J. T.; Yabe, Y.; Gui, J.; Qin, T.; Gutiérrez, S.; Giacoboni, J.; Smith, M. W.; et al. Fe-Catalyzed C—C Bond Construction from Olefins via Radicals. J. Am. Chem. Soc. 2017, 139 (6), 2484-2503. https://doi.org/10.1021/jacs.6b13155.

(21) Kim, D.; Rahaman, S. M. W.; Mercado, B. Q.; Poli, R.; Holland, P. L. Roles of Iron Complexes in Catalytic Radical Alkene Cross-Coupling: A Computational and Mechanistic Study. J. Am. Chem. Soc. 2019, 141 (18), 7473-7485. https://doi.org/10.1021/jacs.9b02117.

(22) Crockett, M. P.; Tyrol, C. C.; Wong, A. S.; Li, B.; Byers, J. A. Iron-Catalyzed Suzuki-Miyaura Cross-Coupling Reactions between Alkyl Halides and Unactivated Arylboronic Esters. Org. Lett. 2018, 20 (17), 5233-5237. https://doi.org/10.1021/acs.orglett.8b02184.

(23) Hatakeyama, T.; Hashimoto, T.; Kondo, Y.; Fujiwara, Y.; Seike, H.; Takaya, H.; Tamada, Y.; Ono, T.; Nakamura, M. Iron-Catalyzed Suzuki-Miyaura Coupling of Alkyl Halides. J. Am. Chem. Soc. 2010, 132 (31), 10674-10676. https://doi.org/10.1021/ja103973a.

(24) Bedford, R. B.; Brenner, P. B.; Carter, E.; Carvell, T. W.; Cogswell, P. M.; Gallagher, T.; Harvey, J. N.; Murphy, D. M.; Neeve, E. C.; Nunn, J.; et al. Expedient Iron-Catalyzed Coupling of Alkyl, Benzyl and Allyl Halides with Arylboronic Esters. Chem.—A Eur. J. 2014, 20 (26), 7935-7938. https://doi.org/10.1002/chem.201402174

(25) O'Brien, H. M.; Manzotti, M.; Abrams, R. D.; Elorriaga, D.; Sparkes, H. A.; Davis, S. A.; Bedford, R. B. Iron-Catalysed Substrate-Directed Suzuki Biaryl Cross-Coupling. Nat. Catal. 2018, 1 (6), 429-437. https://doi.org/10.1038/s41929-018-0081-x.

(26) Hedström, A.; Izakian, Z.; Vreto, I.; Wallentin, C. J.; Norrby, P. O. On the Radical Nature of Iron-Catalyzed Cross-Coupling Reactions. Chem.—A Eur. J. 2015, 21 (15), 5946-5953. https://doi.org/10.1002/chem.201406096.

(27) Daifuku, S. L.; Al-Afyouni, M. H.; Snyder, B. E. R.; Kneebone, J. L.; Neidig, M. L. A Combined Mössbauer, Magnetic Circular Dichroism, and Density Functional Theory Approach for Iron Cross-Coupling Catalysis: Electronic Structure, in Situ Formation, and Reactivity of Iron-Mesityl-Bisphosphines. J. Am. Chem. Soc. 2014, 136 (25), 9132-9143. https://doi.org/10.1021/ja503596m.

(28) Daifuku, S. L.; Kneebone, J. L.; Snyder, B. E. R.; Neidig, M. L. Iron(II) Active Species in Iron-Bisphosphine Catalyzed Kumada and Suzuki-Miyaura Cross-Couplings of Phenyl Nucleophiles and Secondary Alkyl Halides. J. Am. Chem. Soc. 2015, 137 (35), 11432-11444. https://doi.org/10.1021/jacs.5b06648.

(29) Tyrol, C. C.; Yone, N. S.; Gallin, C. F.; Byers, J. A. Iron-Catalysed Enantioconvergent Suzuki-Miyaura Cross-Coupling to Afford Enantioenriched 1,1-Diarylalkanes. Chem. Commun. 2020, 56 (93), 14661-14664. https://doi.org/10.1039/D0CC05003B.

(30) Fürstner, A. Iron Catalysis in Organic Synthesis: A Critical Assessment of What It Takes to Make This Base Metal a Multitasking Champion. ACS Cent. Sci. 2016, 2 (11), 778-789. https://doi.org/10.1021/acscentsci.6b00272.

(31) Crockett, M. P.; Wong, A. S.; Li, B.; Byers, J. A. Rational Design of an Iron-Based Catalyst for Suzuki-Miyaura Cross-Couplings Involving Heteroaromatic Boronic Esters and Tertiary Alkyl Electrophiles. Angew. Chemie Int. Ed. 2020, 59 (13), 5392-5397. https://doi.org/10.1002/anie.201914315.

(32) Eckert, N. A.; Smith, J. M.; Lachicotte, R. J.; Holland, P. L. Low-Coordinate Iron(II) Amido Complexes of β-Diketiminates: Synthesis, Structure, and Reactivity. Inorg. Chem. 2004, 43 (10), 3306-3321. https://doi.org/10.1021/ic035483x.

(33) Cowley, R. E.; Deyonker, N. J.; Eckert, N. A.; Cundari, T. R.; Debeer, S.; Bill, E.; Ottenwaelder, X.; Flaschenriem, C.; Holland, P. L. Three-Coordinate Terminal Imidoiron(III) Complexes: Structure, Spectroscopy, and Mechanism of Formation. Inorg. Chem. 2010, 49 (13), 6172-6187. https://doi.org/10.1021/ic100846b.

(34) Cowley, R. E.; Eckert, N. A.; Vaddadi, S.; Figg, T. M.; Cundari, T. R.; Holland, P. L. Selectivity and Mechanism of Hydrogen Atom Transfer by an Isolable Imidoiron(III) Complex. J. Am. Chem. Soc. 2011, 133 (25), 9796-9811. https://doi.org/10.1021/ja2005303.

(35) Cowley, R. E.; Holland, P. L. Ligand Effects on Hydrogen Atom Transfer from Hydrocarbons to Three-Coordinate Iron Imides. Inorg. Chem. 2012, 51 (15), 8352-8361. https://doi.org/10.1021/ic300870y.

(36) Hu, M. L.; Miao, Q.; Fang, L. P.; Jin, Z. M. Crystal Structure of Tris(Acetylacetonato)Iron(III), C15H21O6Fe, at 20 K. Zeitschrift fur Krist.—New Cryst. Struct. 2001, 216 (1-4), 631-632. https://doi.org/10.1524/ncrs.2001.216.14.631.

(37) Wertheim, G. K.; Kingston, W. R.; Herber, R. H. Mössbauer Effect in Iron (III) Acetylacetonate and Chemical Consequences of K Capture in Cobalt (III) Acetylacetonate. J. Chem. Phys. 1962, 37 (4), 687-690. https://doi.org/10.1063/1.1733147.

(38) Korendovych, I. V.; Staples, R. J.; Reiff, W. M.; Rybak-Akimova, E. V. A New High-Spin Iron(III) Complex with a Pentadentate Macrocyclic Amidopyridine Ligand: A Change from Slow Single-Ion Paramagnetic Relaxation to Long-Range Antiferromagnetic Order in a Hydrogen-Bonded Network. Inorg. Chem. 2004, 43 (13), 3930-3941. https://doi.org/10.1021/ic0351601.

(39) Lithium amides are pyrophoric when exposed to air.

(40) Burger, B. J.; Bercaw, J. E. Vacuum Line Techniques for Handling Air-Sensitive Organometallic Compounds. In Experimental Organometallic Chemistry; American Chemical Society, 1987; pp 79-115. https://doi.org/10.1021/bk-1987-0357.ch004.

(41) Pangborn, A. B.; Giardello, M. A.; Grubbs, R. H.; Rosen, R. K.; Timmers, F. J. Safe and Convenient Procedure for Solvent Purification. Organometallics 1996, 15 (5), 1518-1520. https://doi.org/10.1021/om9503712.

(42) Evans, D. F. The Determination of the Paramagnetic Susceptibility of Substances in Solution by Nuclear Magnetic Resonance. J. Chem. Soc. 1959, 2003-2005. https://doi.org/10.1039/jr9590002003.

(43) Ackermann, L.; Kapdi, A. R.; Schulzke, C. Air-Stable Secondary Phosphine Oxide or Chloride (Pre)Ligands for Cross-Couplings of Unactivated Alkyl Chlorides. Org. Lett. 2010, 12 (10), 2298-2301. https://doi.org/10.1021/ol100658y.

What is claimed:

1. An iron(III) catalyst for Suzuki-Miyaura cross-coupling reactions, wherein the catalyst has a composition according to Formula 1:

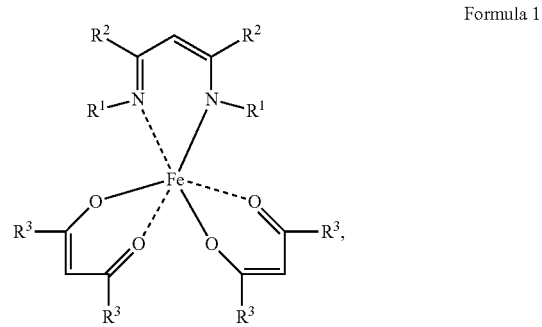

Formula 1 wherein:
each $R^1$ is independently selected from the group consisting of H, an alkyl group having 1 to 5 carbon atoms, cyclopentyl, cyclopropyl, $CF_3$, or phenyl, and an alkyl substituted aryl group wherein the alkyl group has 1 to 5 carbon atoms;

each $R^2$ is independently selected from the group consisting of an alkyl group having 1 to 5 carbon atoms, cyclopentyl, cyclopropyl, $CF_3$, phenyl, and an alkyl substituted aryl group wherein the alkyl group has 1 to 5 carbon atom; and each $R^3$ is independently selected from the group consisting of an alkyl group having 1 to 5 carbon atoms, cyclopentyl, cyclopropyl, $CF_3$, phenyl, and an alkyl substituted aryl wherein the alkyl group has 1 to 5 carbon atoms.

2. The iron(III) catalyst according to claim 1, wherein $R^1$, $R^2$ or $R^3$ each is independently selected from the group consisting of methyl, ethyl, propyl, butyl, pentyl, isopropyl, neopentyl, tert-butyl, cyclopentyl, cyclopropyl, and $CF_3$.

3. The iron(III) catalyst according to claim 1, wherein the alkyl substituted aryl group of $R^1$, $R^2$, or $R^3$ is selected from the group consisting of 2,6-dialkyl substituted aryl, 3,5-dialkyl substituted aryl, and 2,4,6-trialkyl substituted aryl.

4. The iron(III) catalyst according to claim 3, wherein for the alkyl group of the dialkyl and trialkyl substituted aryl groups, the alkyl group is selected from the group consisting of methyl, ethyl, propyl, butyl, pentyl, isopropyl, neopentyl, and tert-butyl.

5. An iron(III) catalyst-for Suzuki-Miyaura cross-coupling reactions, wherein the catalyst has a composition according to Formula 1:

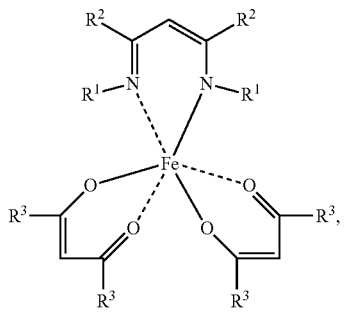

Formula 1 wherein:
each $R^1$ is independently selected from the group consisting of H, an alkyl group having 1 to 5 carbon atoms, cyclopentyl, cyclopropyl, $CF_3$, phenyl, and a substituted aryl group;
each $R_2$ is independently selected from the group consisting of an alkyl group having 1 to 5 carbon atoms, cyclopentyl, cyclopropyl, $CF_3$, phenyl, and a substituted aryl group; and
each $R^3$ is independently selected from the group consisting of an alkyl group having 1 to 5 carbon atoms, cyclopentyl, cyclopropyl, $CF_3$, phenyl, and a substituted aryl,
wherein the substituted aryl group is selected from the group consisting of 2,6-dialkyl substituted aryl, 3,5-dialkyl substituted aryl, 2,4,6-trialkyl substituted aryl, and 2,4,6-trisubstituted aryl, wherein in the 2,4,6-trisubstituted aryl groups a 2-substituent and a 6-substituent are each independently selected from the group consisting of methyl, ethyl, propyl, butyl, pentyl, isopropyl, neopentyl, tert-butyl, cyclopentyl, cyclopropyl, and $CF_3$, and a 4-substituent is selected from the group consisting of a halogen, an alkyl ether, and a dialkyl amine, wherein the alkyl comprises a group selected from methyl, ethyl, propyl, butyl, pentyl, isopropyl, neopentyl, tert-butyl, cyclopentyl, cyclopropyl, and $CF_3$.

6. The iron(III) catalyst according to claim 1, wherein the iron(III) catalyst has a composition according to Formula 2:

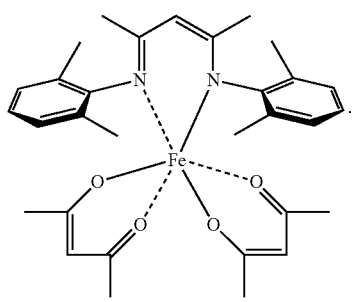

Formula 2

7. The iron(III) catalyst according to claim 1, wherein the catalyst is stable in a solid state for a period of time selected from three to six months; three to nine months, six to nine months, each when stored in a desiccator.

8. A method of making an iron(III) catalyst for Suzuki-Miyaura cross-coupling reactions comprising the steps of:
preparing a solution of an $Fe(acac)_3$ complex;
reacting a β-diketimine compound with butyllithium to form a β-diketiminate;
mixing the β-diketiminate and the solution of an $Fe(acac)_3$ complex to form the iron(III) catalyst having a composition according to Formula 1:

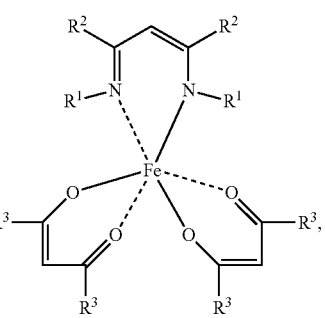

Formula 1 wherein;
each $R^1$ is independently selected from the group consisting of H, an alkyl group having 1 to 5 carbon atoms, cyclopentyl, cyclopropyl, $CF_3$, phenyl, and an alkyl substituted aryl group wherein the alkyl group has 1 to 5 carbon atoms;
each $R^2$ is independently selected from the group consisting of an alkyl group having 1 to 5 carbon atoms, cyclopentyl, cyclopropyl, $CF_3$, phenyl, and an alkyl substituted aryl group wherein the alkyl group has 1 to 5 carbon atom; and
each $R^3$ is independently selected from the group consisting of an alkyl group having 1 to 5 carbon atoms, cyclopentyl, cyclopropyl, $CF_3$, phenyl, and an alkyl substituted aryl wherein the alkyl group has 1 to 5 carbon atoms.

9. The method according to claim 8, wherein the β-diketimine compound is 2,4-bis[(2,6-dimethylphenyl)imino]pentane.

10. The method according to claim 8, wherein the iron(III) catalyst has a composition according to Formula 2:

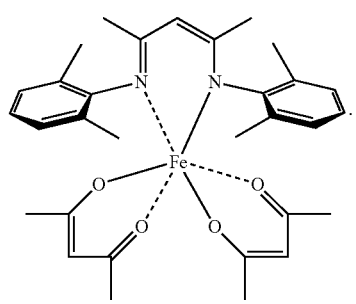

Formula 2

11. A method of catalyzing Suzuki-Miyaura cross-coupling reaction, comprising contacting a compound A of formula $R^A$—X and a compound B of formula $R^B$-G with the iron(III) catalyst according to claim 1, wherein $R^A$ is selected from the group consisting of alkyl, cyclopropyl, and cyclopentyl; X is halogen; $R^B$ is an aryl or heteroaryl; and G is $B(OH)_2$ or esters thereof.

12. The method according to claim 11, wherein the $R^A$ is a primary alkyl selected from the group consisting of methyl, ethyl, propyl, butyl, and pentyl.

13. The method according to claim 11, wherein the $R^A$ is selected from the group consisting of isopropyl, 2-butyl, cyclopentyl, and cyclopropyl.

14. The method according to claim 11, wherein the $R^A$ is a tertiary alkyl selected from the group consisting of t-butyl and 2-(2-methyl)-butyl.

15. The method according to claim 12, wherein X is Br or I.

16. The method according to claim 12, wherein $R^B$ is phenyl, 2-pyridinyl, 3-pyridinyl, or 4-pyridinyl.

17. The method according to claim 11, wherein $R^B$-G is selected from the group consisting of 2-thiophenyl boronic acid pinacol ester, 3-thiophenyl boronic acid pinacol ester, (3-(trifluoromethyl)phenyl) boronic acid pinacol ester, 3-furyl boronic acid pinacol ester, 6-quinolyl boronic acid pinacol ester, 6-(4-Boc-piperazin-1-yl)pyridine-3-boronic acid pinacol ester, (4-methoxyphenyl) boronic acid pinacol ester, and phenyl boronic acid pinacol ester.

18. The method according to claim 11, wherein the iron(III) catalyst according to claim 1 is employed at 10 mole percent of $R^A$—X.

19. The method according to claim 11, wherein the iron(III) catalyst according to claim 1 is employed at 20 mole percent of $R^A$—X.

20. The method according to claim 11, wherein the iron(III) catalyst according to claim 1 is employed at 5 mole percent of $R^A$—X.

* * * * *